US012773178B2

(12) United States Patent
Ye et al.

(10) Patent No.: US 12,773,178 B2
(45) Date of Patent: Oct. 27, 2026

(54) SYSTEMS AND METHODS FOR MEDICAL IMAGING

(71) Applicant: SHANGHAI UNITED IMAGING HEALTHCARE CO., LTD., Shanghai (CN)

(72) Inventors: Qing Ye, Shanghai (CN); Yinghan Qu, Shanghai (CN); Yizhang Zhao, Shanghai (CN); Xiaoyue Gu, Shanghai (CN); Qiujing Xiang, Shanghai (CN); Hancong Xu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 204 days.

(21) Appl. No.: 18/540,808

(22) Filed: Dec. 14, 2023

(65) Prior Publication Data

US 2024/0156426 A1 May 16, 2024

Related U.S. Application Data

(63) Continuation of application No. PCT/CN2022/129328, filed on Nov. 2, 2022.

(30) Foreign Application Priority Data

Nov. 2, 2021 (CN) ......................... 202111290692.4
Dec. 29, 2021 (CN) ......................... 202111646992.1
Dec. 31, 2021 (CN) ......................... 202111678287.X

(51) Int. Cl.
*A61B 6/00* (2024.01)
*A61B 6/03* (2006.01)

(52) U.S. Cl.
CPC ................ *A61B 6/54* (2013.01); *A61B 6/037* (2013.01); *A61B 6/488* (2013.01)

(58) Field of Classification Search
CPC ........... A61B 6/54; A61B 6/037; A61B 6/488; A61B 6/481; A61B 6/469
See application file for complete search history.

(56) References Cited

U.S. PATENT DOCUMENTS 6,337,992 B1 1/2002 Gelman
6,408,201 B1 6/2002 Foo et al.
(Continued)

FOREIGN PATENT DOCUMENTS

CN 107789001 A 3/2018
CN 108182434 A 6/2018
(Continued)

OTHER PUBLICATIONS

Wang, Feng et al., Study of Time-of-flight Influence on Image Quality by PET/CT Scanner, Chinese Medical Equipment Journal, 34(1): 8-11, 2013.

(Continued)

*Primary Examiner* — Peter Luong
(74) *Attorney, Agent, or Firm* — METIS IP LLC

(57) ABSTRACT

The present disclosure relates to systems and methods for medical imaging. The systems may obtain an initial image of an object. The initial image may include a first region of interest (ROI) and one or more second ROIs. The systems may determine, based on the initial image, a first position corresponding to the first ROI and one or more second positions each of which corresponds to one of the one or more second ROIs. The systems may obtain scan data of the object by causing an imaging device to scan the object based on the first position and the one or more second positions. The systems may determine an injection parameter of a drug that is injected into the object based on the scan data. The systems may generate a target image of the object based on the injection parameter and the scan data of the object.

18 Claims, 15 Drawing Sheets

(56) References Cited

U.S. PATENT DOCUMENTS

| | | | | |
|---|---|---|---|---|
| 7,381,959 | B2 | 6/2008 | Manjeshwar et al. | |
| 9,872,664 | B1 | 1/2018 | Jin et al. | |
| 10,213,174 | B1 | 2/2019 | Grobshtein et al. | |
| 2005/0187462 | A1 * | 8/2005 | Koh | A61B 6/481 600/416 |
| 2007/0239416 | A1 | 10/2007 | Saito et al. | |
| 2010/0054559 | A1 | 3/2010 | Narayanan | |
| 2011/0208046 | A1 * | 8/2011 | Gonzalez Molezzi | G16H 30/20 600/431 |
| 2011/0299747 | A1 | 12/2011 | Solf et al. | |
| 2012/0098671 | A1 | 4/2012 | Wieczorek et al. | |
| 2013/0109964 | A1 | 5/2013 | Kelly | |
| 2013/0261441 | A1 | 10/2013 | Das et al. | |
| 2013/0322717 | A1 | 12/2013 | Bar-Shalev | |
| 2014/0153690 | A1 | 6/2014 | Claus et al. | |
| 2014/0185780 | A1 | 7/2014 | Zhao et al. | |
| 2014/0270443 | A1 | 9/2014 | Vija | |
| 2017/0000440 | A1 | 1/2017 | Okerlund et al. | |
| 2017/0053423 | A1 | 2/2017 | Ahn et al. | |
| 2018/0071452 | A1 | 3/2018 | Sharma et al. | |
| 2018/0184992 | A1 | 7/2018 | Li et al. | |
| 2018/0289340 | A1 | 10/2018 | Trindade Rodrigues et al. | |
| 2019/0167213 | A1 | 6/2019 | Jain et al. | |
| 2020/0037975 | A1 | 2/2020 | Zhu et al. | |
| 2020/0245894 | A1 | 8/2020 | Shi et al. | |
| 2020/0311456 | A1 | 10/2020 | Ji et al. | |
| 2020/0352537 | A1 | 11/2020 | Bai et al. | |
| 2021/0128820 | A1 | 5/2021 | Vaz et al. | |
| 2021/0295501 | A1 | 9/2021 | Hu et al. | |

FOREIGN PATENT DOCUMENTS

| | | | |
|---|---|---|---|
| CN | 108606806 | A | 10/2018 |
| CN | 109381212 | A | 2/2019 |
| CN | 109567843 | A | 4/2019 |
| CN | 110400361 | A | 11/2019 |
| CN | 112017258 | A | 12/2020 |
| CN | 113065017 | A | 7/2021 |
| CN | 114010212 | A | 2/2022 |
| CN | 114209430 | A | 3/2022 |
| CN | 114259247 | A | 4/2022 |
| JP | 2012020174 | A | 2/2012 |
| WO | 2009147605 | A1 | 12/2009 |
| WO | 2010056900 | A1 | 5/2010 |
| WO | 2014047446 | A1 | 3/2014 |

OTHER PUBLICATIONS

International Search Report in PCT/CN2022/129328 mailed on Jan. 12, 2023, 5 pages.

Written Opinion in PCT/CN2022/129328 mailed on Jan. 12, 2023, 5 pages.

Shu, Jun et al., Effect and Countermeasures of Delayed Acquisition Time on SUV in FDG/PET, Journal of Information Engineering University, 16(4): 454-457, 2015.

The Extended European Search Report in European Application No. 22889330.1 mailed on Sep. 17, 2024, 6 pages.

Wang, Shaobo et al., Feasibility of perfusion and early-uptake 18F-FDG PET/CT in primary hepatocellular carcinoma: a dual-input dual-compartment uptake model, Japanese Journal of Radiology, 2021, 11 pages.

Communication Pursuant to Article 94(3) EPC in European Application No. 22889330.1 mailed on Jun. 4, 2025, 5 pages.

The Second Office Action in Chinese Application No. 202111290692.4 mailed on Jun. 28, 2025, 18 pages.

Decision to Grant a Patent in Chinese Application No. 202311658988.6 mailed on Apr. 14, 2026, 21 pages.

First Examination Report in Indian Application No. 202317085108 mailed on Mar. 20, 2026, 7 pages.

* cited by examiner

1100A

1100B

1100C

1200

1400

1500

SYSTEMS AND METHODS FOR MEDICAL IMAGING

CROSS-REFERENCE TO RELATED APPLICATIONS

This application is a continuation of International Application No. PCT/CN2022/129328, filed on Nov. 2, 2022, which claims priority of Chinese Patent Application No. 202111290692.4 filed on Nov. 2, 2021, Chinese Patent Application No. 202111646992.1 filed on Dec. 29, 2021, and Chinese Patent Application No. 202111678287.X filed on Dec. 31, 2021, the contents of each of which are incorporated herein by reference.

TECHNICAL FIELD

The present disclosure generally relates to medical imaging, and in particular, to systems and methods for positron emission tomography (PET) imaging.

BACKGROUND

PET imaging has been widely used in clinical examination and disease diagnosis in recent years. In particular, dynamic PET imaging can provide a set of images over a dynamic scan time and dynamic PET data can also provide rich information related to physiological parameters (e.g., perfusion pressure) that indicate the functional status of the imaged tissue(s) or organ(s). However, it is difficult to accurately control the dynamic PET imaging process, for example, how to accurately position ROIs, how to accurately determine injection dose, how to accurately and efficiently generate a final image, etc. Therefore, it is desirable to provide systems and methods for medical imaging to accurately control the dynamic PET imaging process.

SUMMARY

An aspect of the present disclosure relates to a system for medical imaging. The system may include at least one storage device including a set of instructions and at least one processor in communication with the at least one storage device. When executing the set of instructions, the at least one processor may be directed to perform operations. The operations may include obtaining an initial image of an object. The initial image may include a first region of interest (ROI) and one or more second ROIs. The operations may include determining, based on the initial image, a first position corresponding to the first ROI and one or more second positions each of which corresponds to one of the one or more second ROIs. The operations may include obtaining scan data of the object by causing an imaging device to scan the object based on the first position and the one or more second positions. The operations may include determining an injection parameter of a drug that is injected into the object based on the scan data. The operations may further include generating a target image of the object based on the injection parameter and the scan data of the object.

In some embodiments, the obtaining the scan data of the object by causing the imaging device to scan the object based on the first position and the one or more second positions may include determining a scan plan based on the first position and the one or more second positions and obtaining the scan data of the object by causing the imaging device to scan the object based on the scan plan. The scan plan at least may include a scan parameter associated with an overlapping region of scanning regions corresponding to two adjacent second ROIs.

In some embodiments, the obtaining the scan data of the object by causing the imaging device to scan the object based on the first position and the one or more second positions may include.

In some embodiments, determining a scan plan based on the first position, the one or more second positions, and a parameter associated with the drug and obtaining the scan data of the object by causing the imaging device to scan the object based on the scan plan. The scan plan at least may include a moving speed of the object among the first position and the one or more second positions.

In some embodiments, the determining the injection parameter of the drug that is injected into the object based on the scan data may include determining a count of coincidence events for the object based on the scan data and determining an injection dose of the drug based on the count of the coincidence events. A coincidence event may indicate a pair of photons detected by detectors surrounding the object within a preset time window.

In some embodiments, the determining the count of the coincidence events may include determining the count of the coincidence events by correcting an initial count of the coincidence events based on a decay correction function.

In some embodiments, the determining the injection parameter of the drug that is injected into the object based on the scan data may include determining a plurality of initial reconstruction images based on at least a portion of the scan data according to a preset temporal frequency and determining an injection time of the drug based on the plurality of initial reconstruction images.

In some embodiments, the determining the injection time of the drug based on the plurality of initial reconstruction images include for each of the plurality of initial reconstruction images, determining pixel values associated with a target region; determining, from the plurality of initial reconstruction images, a target reconstruction image based on the pixel values corresponding to the plurality of initial reconstruction images respectively, the target reconstruction image corresponding to target pixel values indicating that the target reconstruction image is the first image, among the plurality of initial reconstruction images, that indicates an occurrence of the drug; and designating an acquisition time associated with the target reconstruction image as the injection time of the drug.

In some embodiments, the generating the target image of the object based on the injection parameter and the scan data of the object may include generating the target image of the object based on the injection parameter, the scan data of the object, and a target model. The target model may include at least one of a reconstruction algorithm, a reconstruction model, or a kinetic model. The kinetic model may indicate a metabolism situation of the drug injected into the object.

In some embodiments, the operations may further include causing a display device to display a first interface. The first interface may include a plurality of preset models each of which indicates a conversion relationship among parameters of the preset model. the operations may further include determining, in response to a trigger instruction, the target model from the plurality of preset models and causing the display device to display a second interface based on the target model. The second interface may include at least one region used to display at least one parameter image each of which is related to a parameter of the target model.

In some embodiments, the plurality of preset models may include a compartment model. The compartment model may include at least one of a two-compartment model, a three-compartment model, or a four-compartment model.

A further aspect of the present disclosure relates to a method for medical imaging. The method may be implemented on a computing device including at least one processor and at least one storage device. The method may include obtaining an initial image of an object. The initial image may include a first region of interest (ROI) and one or more second ROIs. The method may include determining, based on the initial image, a first position corresponding to the first ROI and one or more second positions each of which corresponds to one of the one or more second ROIs. The method may include obtaining scan data of the object by causing an imaging device to scan the object based on the first position and the one or more second positions. The method may include determining an injection parameter of a drug that is injected into the object based on the scan data. The method may further include generating a target image of the object based on the injection parameter and the scan data of the object.

A still further aspect of the present disclosure relates to a non-transitory computer readable medium including executable instructions. When the executable instructions are executed by at least one processor, the executable instructions may direct the at least one processor to perform a method. The method may include obtaining an initial image of an object. The initial image may include a first region of interest (ROI) and one or more second ROIs. The method may include determining, based on the initial image, a first position corresponding to the first ROI and one or more second positions each of which corresponds to one of the one or more second ROIs. The method may include obtaining scan data of the object by causing an imaging device to scan the object based on the first position and the one or more second positions. The method may include determining an injection parameter of a drug that is injected into the object based on the scan data. The method may further include generating a target image of the object based on the injection parameter and the scan data of the object.

A further aspect of the present disclosure relates to medical imaging. The system may include at least one storage device including a set of instructions and at least one processor in communication with the at least one storage device. When executing the set of instructions, the at least one processor may be directed to perform operations. The operations may include obtaining an initial image of an object. The initial image may include a first region of interest (ROI) and one or more second ROIs. The operations may include determining, based on the initial image, a first position corresponding to the first ROI and one or more second positions each of which corresponds to one of the one or more second ROIs. The operations may include determining a scan plan based on the first position and the one or more second positions. The operations may further include obtaining scan data of the object by causing an imaging device to scan the object based on the scan plan.

A further aspect of the present disclosure relates to medical imaging. The system may include at least one storage device including a set of instructions and at least one processor in communication with the at least one storage device. When executing the set of instructions, the at least one processor may be directed to perform operations. The operations may include obtaining scan data of an object by causing an imaging device to scan the object. The operations may include determining an injection parameter of a drug that is injected into the object based on the scan data. The operations may further include generating a target image of the object based on the injection parameter, the scan data of the object, and a target model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
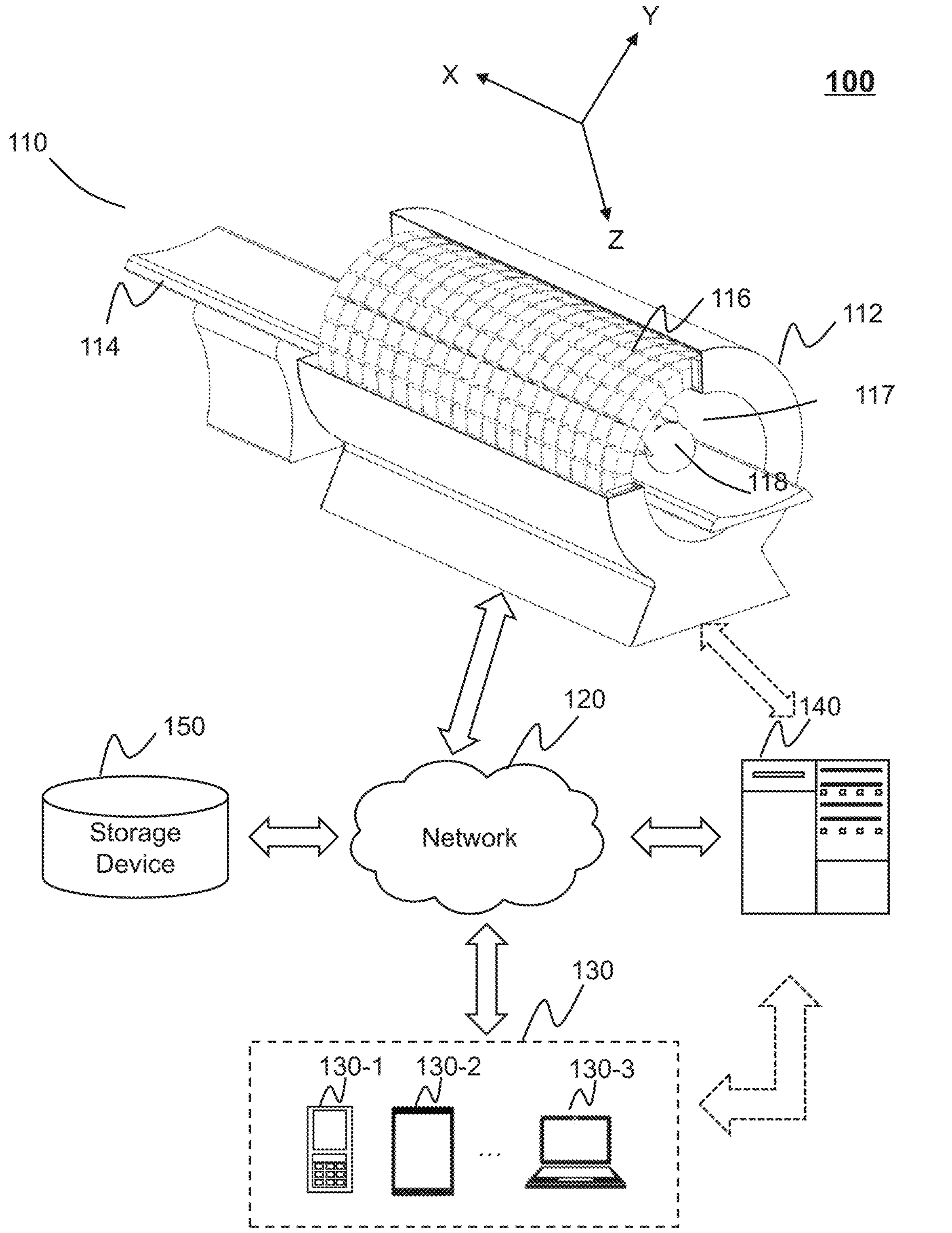
FIG. 1 is a schematic diagram illustrating an exemplary medical imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

The term "image" in the present disclosure is used to collectively refer to imaging data (e.g., scan data, projection data) and/or images of various forms, including a two-dimensional (2D) image, a three-dimensional (3D) image, a four-dimensional (4D), etc. The terms "pixel" and "voxel" in the present disclosure are used interchangeably to refer to an element of an image. The terms "region," "location," and "area" in the present disclosure may refer to a location of an anatomical structure shown in the image or an actual location of the anatomical structure existing in or on a target object's body, since the image may indicate the actual location of a certain anatomical structure existing in or on the target object's body. The terms "object" and "subject" in the present disclosure are used interchangeably to refer to a biological object (e.g., a patient, an animal) or a non-biological object (e.g., a phantom). In some embodiments, the object may include a specific part, organ, and/or tissue of the object. For example, the object may include the head, the bladder, the brain, the neck, the torso, a shoulder, an arm, the thorax, the heart, the stomach, a blood vessel, soft tissue, a knee, a foot, or the like, or any combination thereof, of a patient.

Provided herein are systems and components for non-invasive imaging and/or treatment, such as for disease diagnosis, treatment, or research purposes. In some embodiments, the systems may include a single modality system and/or a multi-modality system. The single modality system may include, for example, a positron emission tomography (PET) system, a single positron emission computed tomography (SPECT) system, etc. The multi-modality system may include, for example, a positron emission tomography-magnetic resonance imaging (PET-MRI) system, a single photon emission computed tomography-magnetic resonance imaging (SPECT-MRI) system, a positron emission tomography-computed tomography (PET-CT) system, a single photon emission computed tomography-computed tomography (SPECT-CT) system, etc. For illustration purposes, the disclosure describes systems and methods for PET.

Generally, a medical imaging system (e.g., a PET system) may acquire scan data (e.g., PET data) relating to an object (e.g., a human body) or a portion thereof (e.g., the object's target tissue(s) or organ(s)) by scanning the object or a portion thereof when a drug (e.g., a tracer species) is injected into the object's body. During the scanning process, a couch where the object is located needs to be controlled to move the object precisely at a right time to a position where the object's target tissue(s) or organ(s) are aligned with a detector of the medical imaging system, so that the object's target tissue(s) or organ(s) can be accurately scanned. The control process is usually executed manually by an operator (e.g., a doctor) based on experience, which results in a large workload and low efficiency and accuracy. In addition, an injection parameter (e.g., an injection time and/or an injection dose) of the drug is usually inputted or determined by the operator manually, which also results in a large workload and low efficiency and accuracy.

Accordingly, an aspect of the present disclosure provides systems and methods for medical imaging. The systems may obtain an initial image (e.g., a scout view) of the object (e.g., a human body). The initial image may include a first region of interest (ROI) (e.g., a blood pool region) and one or more second ROIs (e.g., the object's target tissue or organ). The systems may determine, based on the initial image, a first position corresponding to the first ROI and one or more second positions each of which corresponds to one of the one or more second ROIs. According to the first position and the one or more second positions, the systems may obtain scan data (e.g., PET data) of the object by causing an imaging device (e.g., a PET device) to scan the object. Further, the systems may determine an injection parameter (e.g., the injection time and/or the injection dose) of a drug that is injected into the object based on the scan data and generate a target image (e.g., a PET image) of the object based on the injection parameter and the scan data of the object.

According to some embodiments of the systems and methods of the present disclosure, the first position corresponding to the first ROI (e.g., the blood pool region) and one or more second positions each of which corresponds to one of the one or more second ROIs (e.g., the object's target tissue or organ) may be determined automatically, and the scanning may be automatically performed based on the first position and the one or more second positions, which can reduce the workload of the operator and improve the efficiency and accuracy of the medical imaging. In addition, the systems of the present disclosure can automatically determine the injection time and/or the injection dose of the drug, which avoids the operator manually determining the injection time and/or injection dose, thereby further reducing the workload of the operator and improving the efficiency and accuracy of the medical imaging.

FIG. 1 is a schematic diagram illustrating an exemplary medical imaging system according to some embodiments of the present disclosure. As illustrated in FIG. 1, a medical imaging system 100 may include an imaging device 110, a network 120, a terminal device 130, a processing device 140, and a storage device 150. The components of the medical imaging system 100 may be connected in various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal device 130 (e.g., terminals 130-1, 130-2, 130-3, etc.) may be connected to the processing device 140 directly (as indicated by the bi-directional arrow in dotted lines linking the terminal device 130 and the processing device 140) or through the network 120.

The imaging device 110 may be configured to acquire scan data relating to an object. For example, the imaging device 110 may scan the object or a portion thereof that is located within its detection region and generate scan data relating to the object or the portion thereof. In some embodiments, the imaging device 110 may include a PET device, a SPET device, a PET-MRI device, a SPECT-MRI device, etc.

In some embodiments, the imaging device 110 may include a gantry 112, a couch 114, and a detector module 116. The gantry 112 may support the detector module 116. The couch 114 may be used to support an object 118 to be scanned. The detector module 116 may include one or more detector rings along an axial dimension (e.g., an X-axis direction illustrated in FIG. 1) of the imaging device 110, which form a field of view (FOV) of the imaging device 110. In some embodiments, the field of view (FOV) (e.g., 2 meters) of the imaging device 110 may be greater than or equal to a length of the entire object. In some embodiments, the FOV of the imaging device 110 may be smaller than the length of the entire object. In some embodiments, each of the one or more detector rings may include multiple detectors arranged along the circumference of the detector ring. In some embodiments, the detector may include a scintillation detector (e.g., a cesium iodide detector), a gas detector, or the like, or any combination thereof.

In some embodiments, the object 118 may be moved by moving the couch 114 within a detection region 117 of the imaging device 110. In some embodiments, the couch 114 may move along the axial dimension of the imaging device 110. For example, the couch 114 may move along the positive X-axis direction or the negative X-axis direction. As another example, the couch 114 may move back and forth along the X-axis direction. In some embodiments, the couch 114 may move at a constant velocity or a varying velocity (e.g., a velocity that changes with time). For example, the moving speed of the couch 114 may be 1.5 mm/s for scanning the head of the object; while the moving speed of the couch 114 may be 1.0 for continuously scanning the torso.

In some embodiments, before a scanning (e.g., a PET scanning), the object 118 may be injected with a tracer species. The tracer species may refer to a radioactive substance that decays and emits positrons. In some embodiments, the tracer species may be radioactively marked radiopharmaceutical, which is a drug having radioactivity and is administered to the object 118. For example, the tracer species may include fluorine-18 ($^{18}F$) fluorodeoxyglucose (FDG), etc. During the scanning, pairs of photons (e.g., gamma photons) may result from the annihilation of positrons originating from the tracer species in the object 118. A pair of photons may travel in opposite directions. At least a part of the pairs of photons may be detected and/or registered by the detectors in the detector module 116. A coincidence event may be recorded when a pair of photons generated by the positron-electron annihilation are detected within a coincidence time window (e.g., within 6 to 12 nanoseconds).

The network 120 may facilitate exchange of information and/or data. In some embodiments, one or more components (e.g., the imaging device 110, the terminal device 130, the processing device 140, the storage device 150) of the medical imaging system 100 may send information and/or data to another component(s) of the medical imaging system 100 via the network 120. For example, the processing device 140 may obtain, via the network 120, scan data relating to the object 118 or a portion thereof from the imaging device 110. In some embodiments, the network 120 may be any type of wired or wireless network, or a combination thereof. In some embodiments, the network 120 may include one or more network access points. For example, the network 120 may include wired or wireless network access points such as base stations and/or internet exchange points through which one or more components of the medical imaging system 100 may be connected to the network 120 to exchange data and/or information.

The terminal device 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the terminal device 130 may remotely operate the imaging device 110. In some embodiments, the terminal device 130 may operate the imaging device 110 via a wireless connection. In some embodiments, the terminal device 130 may receive information and/or instructions inputted by a user, and send the received information and/or instructions to the imaging device 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

In some embodiments, the processing device 140 may process data obtained from the imaging device 110, the terminal device 130, or the storage device 150. For example, the processing device 140 may obtain an initial image (e.g., a scout view) of an object (e.g., a human body). The processing device 140 may determine a first position corresponding to a first ROI in the initial image and one or more second positions each of which corresponds to one of one or more second ROIs in the initial image. According to the first position and the one or more second positions, the processing device 140 may obtain scan data (e.g., PET data) of the object by causing the imaging device 110 (e.g., a PET device) to scan the object. Further, the processing device 140 may determine an injection parameter (e.g., the injection time and the injection dose) of a drug (e.g., tracer species) that is injected into the object based on the scan data and generate a target image (e.g., a PET image) of the object based on the injection parameter and the scan data of the object.

In some embodiments, the processing device 140 may be a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the imaging device 110, the terminal device 130, and/or the storage device 150 via the network 120. As another example, the processing device 140 may be directly connected to the imaging device 110, the terminal device 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data and/or instructions. In some embodiments, the storage device 150 may store data obtained from the imaging device 110, the terminal device 130, and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. In some embodiments, the storage device 150 may be implemented on the cloud platform described elsewhere in the present disclosure.

In some embodiments, the storage device 150 may be connected to the network 120 to communicate with one or more components (e.g., the imaging device 110, the terminal device 130, the processing device 140) of the medical imaging system 100. One or more components of the medical imaging system 100 may access the data or instructions stored in the storage device 150 via the network 120. In some embodiments, the storage device 150 may be directly connected to or communicate with one or more components (e.g., the imaging device 110, the terminal device 130, the processing device 140) of the medical imaging system 100. In some embodiments, the storage device 150 may be part of the processing device 140.

It should be noted that the above description of the medical imaging system 100 is merely provided for the purposes of illustration, and not intended to limit the scope of the present disclosure. For persons having ordinary skills in the art, multiple variations and modifications may be made under the teachings of the present disclosure. For example, the medical imaging system 100 may include one or more additional components and/or one or more components of the medical imaging system 100 described above may be omitted. Additionally or alternatively, two or more components of the medical imaging system 100 may be integrated into a single component. A component of the medical imaging system 100 may be implemented on two or more sub-components.

Figure 2:
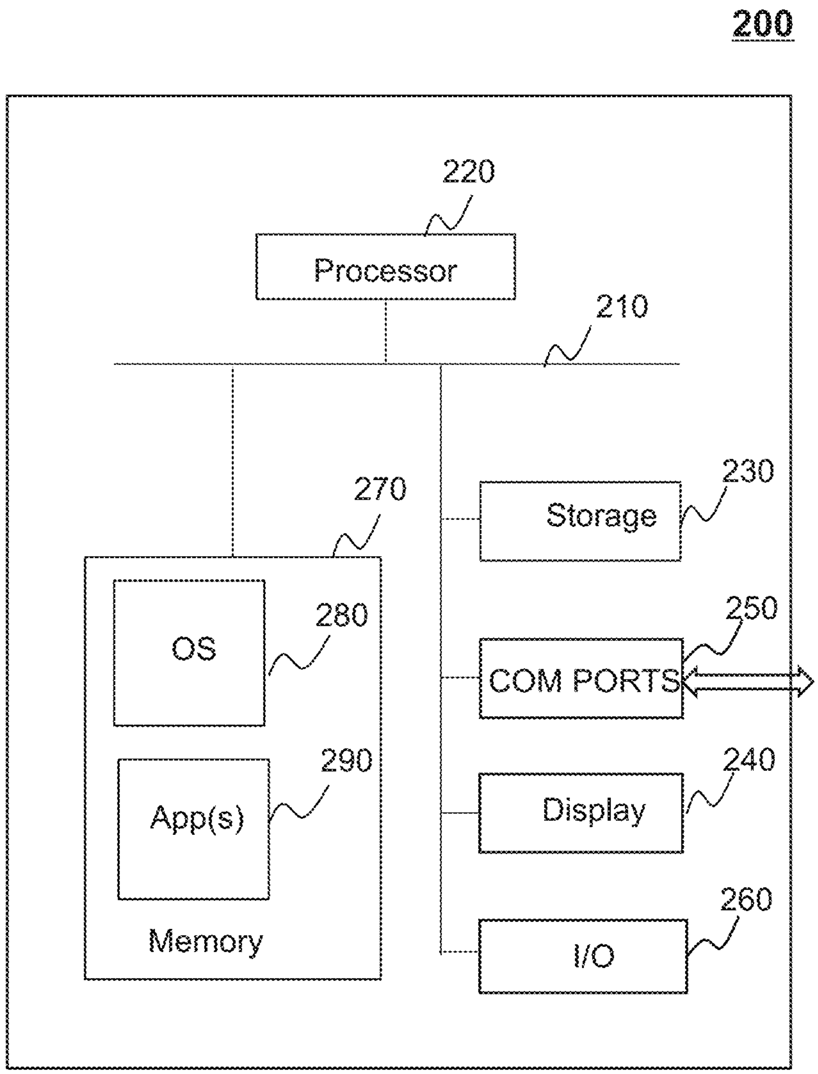
FIG. 2 is a schematic diagram illustrating exemplary hardware and/or software components of an exemplary computing device according to some embodiments of the present disclosure.

FIG. 2 is a schematic diagram illustrating exemplary hardware and/or software components of an exemplary computing device according to some embodiments of the present disclosure. In some embodiments, the processing device 140 may be implemented on the computing device 200. In some embodiments, the computer device 200 may include a terminal or an electronic device. As illustrated in FIG. 2, the computing device 200 may include a data bus 210, a processor 220, a storage 230, a display 240, a communication port 250, an input/output (I/O) 260, and a memory 270.

The data bus 210 may be configured to implement data communications among components of the computing device 200. In some embodiments, hardware of the computing device 200 may transmit data via the data bus 210. For example, the processor 220 may send data to a storage or other hardware such as the I/O 260 via the data bus 210.

The processor 220 may execute computer instructions (program code) and perform functions of the processing device 140 in accordance with techniques described herein. Merely for illustration purposes, only one processor is described in the computing device 200. However, it should be noted that the computing device 200 in the present disclosure may also include multiple processors, and thus operations of a method that are performed by one processor as described in the present disclosure may also be jointly or separately performed by the multiple processors.

The storage 230 may store data/information obtained from the imaging device 110 of the medical imaging system 100. In some embodiments, the storage 230 may store one or more programs and/or instructions to perform exemplary methods described in the present disclosure. In some embodiments, the storage 230 may include an external storage device, for example, a pluggable hard drive, a smart media card, a secure digital, a flash card, or the like, or any combination thereof.

The display 240 may include a light-emitting diode (LED) display, a liquid crystal display screen, an electronic ink display screen, a touch LCD, an organic LED touch, or the like, or any combination thereof. An input device of the computing device 200 may be a touch layer covered on the display 240, or a button, a trackball, or a touchpad set on a shell of the computer device 200, or an external keyboard, trackpad, or mouse connected to the computing device 200.

The communication port 250 may be connected to a network (e.g., the network 120) to facilitate data communications. The communication port 250 may establish connections between the processing device 140 and other components (e.g., the imaging device 110) of the medical imaging system 100. The connection may be a wired connection, a wireless connection, or a combination of both that enables data transmission and reception.

The I/O 260 may input or output signals, data, or information. In some embodiments, the I/O 260 may enable user interaction with the processing device 140. In some embodiments, the I/O 260 may include an input device and an output device. Merely by way of example, a user (e.g., an operator) may input parameters needed for the operation of the imaging device 110.

A mobile operating system 280 (e.g., iOS, Android, Windows Phone) and one or more applications 290 may be loaded into the memory 270 from the storage 230 in order to be executed by the processor 220.

t should be noted that the above description of the computing device 200 is merely provided for the purposes of illustration, and not intended to limit the scope of the present disclosure. For persons having ordinary skills in the art, multiple variations and modifications may be made under the teachings of the present disclosure.

Figure 3:
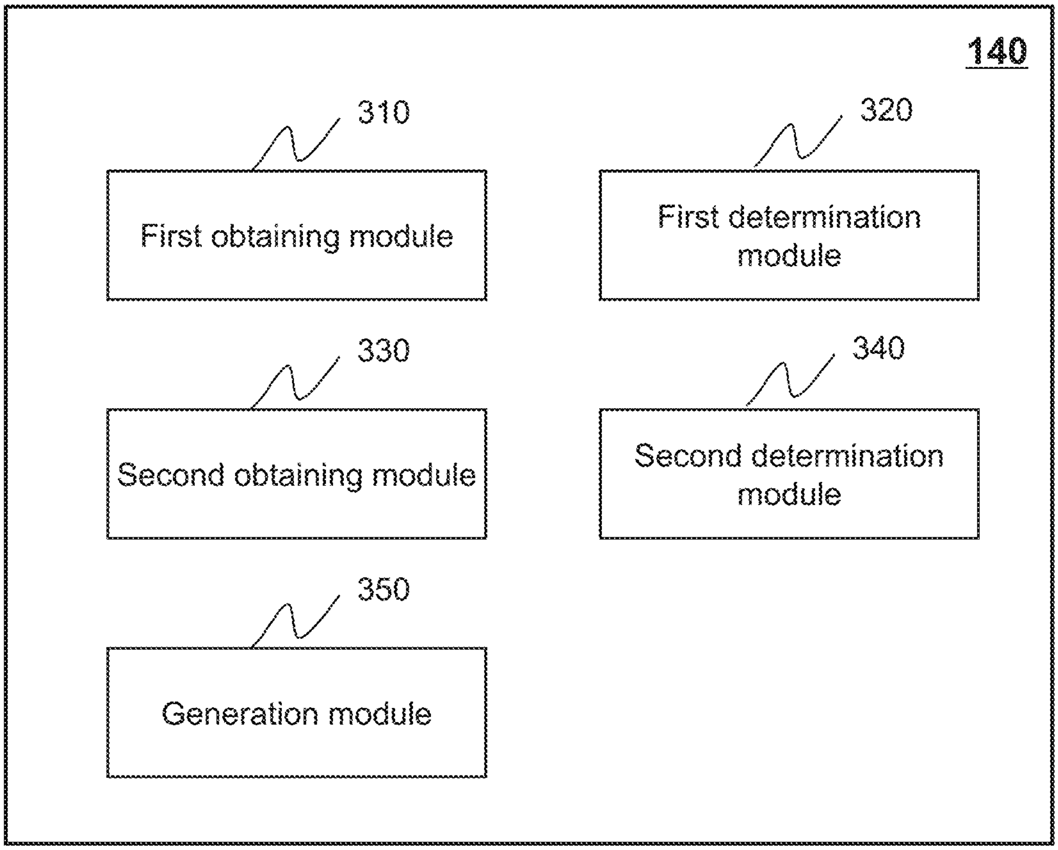
FIG. 3 is a block diagram illustrating an exemplary processing device according to some embodiments of the present disclosure.

FIG. 3 is a block diagram illustrating an exemplary processing device according to some embodiments of the present disclosure. As illustrated in FIG. 3, the processing device 140 may include a first obtaining module 310, a first determination module 320, a second obtaining module 330, a second determination module 340, and a generation module 350.

The first obtaining module 310 may be configured to obtain an initial image (e.g., a scout view) of an object (e.g., a human body). In some embodiments, the initial image may include a first region of interest (ROI) and one or more second ROIs. More descriptions regarding the obtaining of the initial image may be found elsewhere in the present disclosure, for example, operation 410, operation 1610, and the descriptions thereof.

The first determination module 320 may be configured to determine, based on the initial image, a first position corresponding to the first ROI and one or more second positions each of which corresponds to one of the one or more second ROIs. More descriptions regarding the determining of the first position and the one or more second positions may be found elsewhere in the present disclosure, for example, operation 420, operation 1620, and the descriptions thereof.

The second obtaining module 330 may be configured to obtain scan data of the object by causing an imaging device to scan the object based on the first position and the one or more second positions. The second obtaining module 330 may be configured to determine a scan plan based on the first position and the one or more second positions and obtain the scan data of the object by causing the imaging device to scan the object based on the scan plan. The second obtaining module 330 may be configured to obtain the scan data of the object by causing the imaging device to scan the object. More descriptions regarding the obtaining of the scan data of the object may be found elsewhere in the present disclosure, for example, operation 430, operation 1630, operation 1640, operation 1710, and the descriptions thereof.

The second determination module 340 may be configured to determine an injection parameter of the drug that is injected into the object based on the scan data. In some embodiments, the injection parameter of the drug may include an injection dose of the drug, an injection time of the drug, or the like, or a combination thereof. More descriptions regarding the determining of the injection dose and the injection time of the drug may be found elsewhere in the present disclosure, for example, operation 440, FIG. 8, FIG. 9, operation 1720, and the descriptions thereof.

The generation module 350 may be configured to generate a target image of the object based on the injection parameter and the scan data of the object. The generation module 350 may be configured to generate a target image of the object based on the injection parameter, the scan data of the object, and a target model. More descriptions regarding the generation of the target image of the object may be found elsewhere in the present disclosure, for example, operation 450, operation 1730, and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the modules in the processing device 140 may be connected to or communicate with each other via a wired connection or a wireless connection. In some embodiments, two or more of the modules may be combined as a single module, and any one of the modules may be divided into two or more units. For example, the first obtaining module 310 and the second obtaining module 330 may be combined as a single module which may both obtain the initial image and the scan data of the object. As another example, the first determination module 320 and the second determination module 340 may be combined as a single module which may both determine the first position and the one or more second positions and the injection parameter of the drug.

Figure 4:
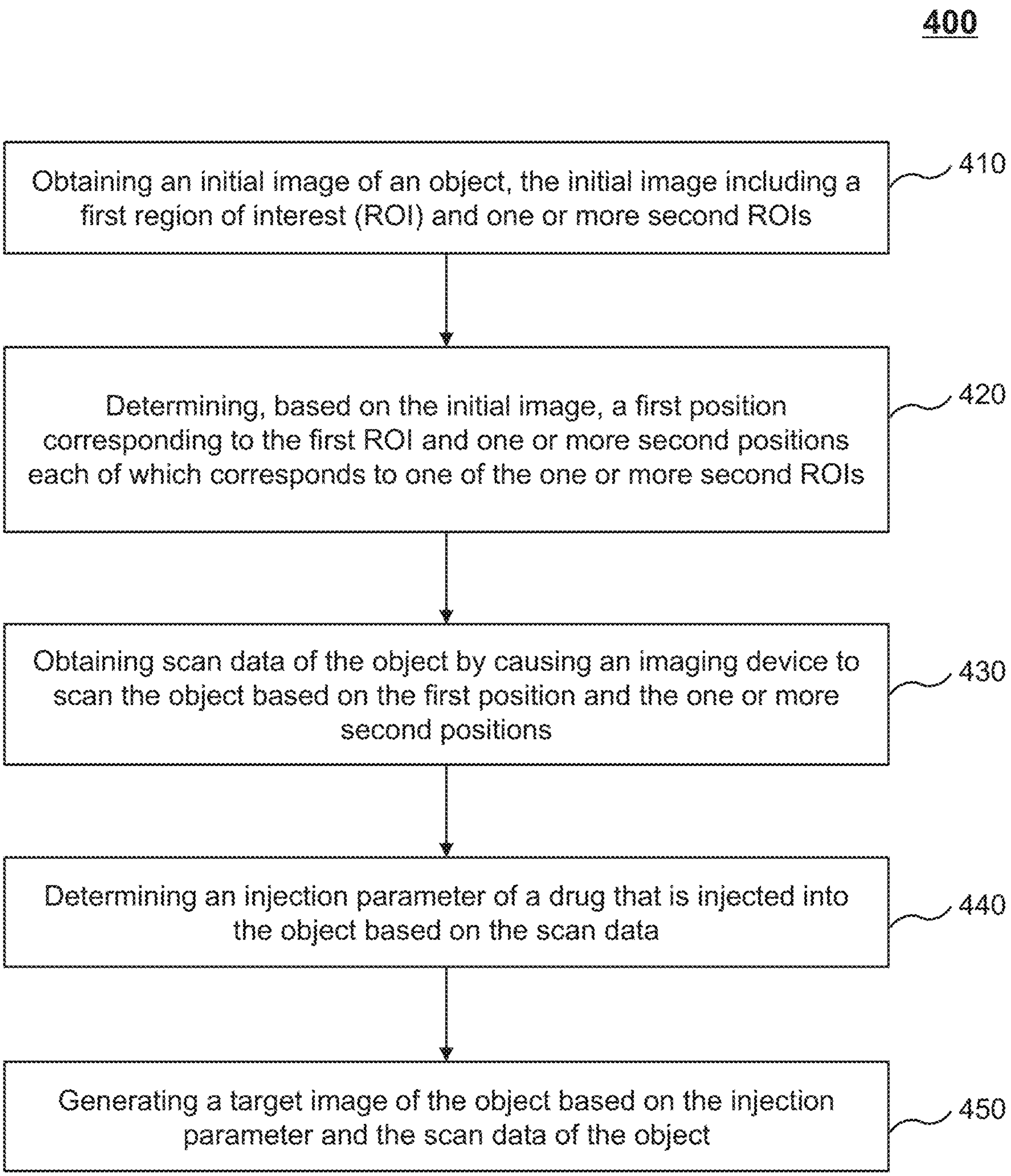
FIG. 4 is a flowchart illustrating an exemplary process for medical imaging according to some embodiments of the present disclosure.

FIG. 4 is a flowchart illustrating an exemplary process for medical imaging according to some embodiments of the present disclosure. In some embodiments, process 400 may be executed by the medical imaging system 100. For example, the process 400 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 400. The operations of the illustrated process presented below are intended to be illustrative. In some embodiments, the process 400 may be accomplished with one or more additional operations not described and/or without one or more of the operations discussed. Additionally, the order of the operations of process 400 illustrated in FIG. 4 and described below is not intended to be limiting.

In 410, the processing device 140 (e.g., the first obtaining module 310 illustrated in FIG. 3, the processor 220 illustrated in FIG. 2) may obtain an initial image (e.g., a scout view) of an object (e.g., a human body).

In some embodiments, the initial image may include a computed tomography (CT) image (e.g., a CT plain scan image), a PET image, a SPECT Image, a radiotherapy radiographic image (e.g., digital radiography), an MR image, an X-ray image, a fluoroscopy image, an ultrasound image, or the like, or a combination thereof.

In some embodiments, the initial image may include a first region of interest (ROI) and one or more second ROIs. The first ROI may be used as a reference for treatment or analysis associated with a tissue or organ. Merely by way of example, the first ROI may include one or more blood pool regions (e.g., aortic blood pools). The one or more second ROIs may include tissue(s) or organ(s) of the object to be scanned according to scan requirements or medical requirements. For example, the one or more second ROIs may include tissue(s) or organ(s) that need treatment and/or other tissue(s) or organ(s) close to the tissue(s) or organ(s) that need treatment. As another example, the one or more second ROIs may include tissue(s) or organ(s) including at least part of a malignant tissue (e.g., a tumor, a cancer-ridden organ, or a non-cancerous target of radiation therapy). As a further example, the one or more second ROIs may include the object's heart, lungs, liver, stomach, pelvis, etc.

In some embodiments, the processing device 140 may determine the first ROI and/or the one or more second ROI in the initial image by using a trained machine learning model. Specifically, the processing device 140 may input the initial image into the trained machine learning model and determine the first ROI and/or the one or more second ROI based on an output of the trained machine learning model. In some embodiments, the trained machine learning model refers to a model or an algorithm for extracting an ROI from an image. Merely by way of example, the trained machine learning model may include a trained neural network model, for example, a deep neural network (DNN) model, a convolutional neural network (CNN) model, a recurrent neural network (RNN) model, a feature pyramid network (FPN) model, or the like, or any combination thereof.

In some embodiments, the trained machine learning model may include an image segmentation algorithm. Exemplary image segmentation algorithm may include a thresholding segmentation algorithm, a compression-based algorithm, an edge detection algorithm, a machine learning-based segmentation algorithm, or the like, or any combination thereof. Exemplary machine learning-based segmentation algorithms may include a 3D U-Net algorithm, a Res-UNet algorithm, a Dense-UNet algorithm, a CNN-based recursive residual image segmentation network algorithm, etc.

In some embodiments, the first ROI and/or the one or more second ROI in the initial image may be manually determined by an operator (e.g., a doctor). For example, the operator may manually sketch the first ROI and/or the one or more second ROI in the initial image via a user interface. In some embodiments, the first ROI and/or the one or more second ROI may be segmented from the initial image by the processing device 140 automatically using an image segmentation algorithm. Exemplary image segmentation algorithm may include a thresholding segmentation algorithm, a compression-based algorithm, an edge detection algorithm, a machine learning-based segmentation algorithm, or the like, or any combination thereof.

In some embodiments, the processing device 140 may direct the imaging device 110 to perform a scan (e.g., a PET scan) on the object and determine the initial image based on scanning data obtained from the imaging device 110. In some embodiments, the initial image may be previously determined and stored in a storage device (e.g., the storage device 150, the storage 230, an external storage device) or an external system (e.g., a picture archiving and communication system (PACS)). The processing device 140 may obtain the initial image from the storage device or the external system directly or via a network (e.g., the network 120).

In 420, the processing device 140 (e.g., the first determination module 320 illustrated in FIG. 3, the processor 220 illustrated in FIG. 2) may determine, based on the initial image, a first position corresponding to the first ROI and one or more second positions each of which corresponds to one of the one or more second ROIs.

In some embodiments, the first position or the second position refers to a position of a couch (e.g., the couch 114) on which the object is supported relative to an imaging device (e.g., the imaging device 110). The first position may be a scanning position (e.g., an optimal scanning position (e.g., a center of a scanning FOV of the imaging device)) for the imaging device to scan the first ROI. The second position may be a scanning position (e.g., an optimal scanning position (e.g., a center of a scanning FOV of the imaging device)) for the imaging device to scan a corresponding second ROI.

In some embodiments, the processing device 140 may determine the first position and/or the one or more second positions by using a trained machine learning model. Specifically, the processing device 140 may input the initial image into the trained machine learning model and determine the first position and/or the one or more second positions based on an output of the trained machine learning model.

In 430, the processing device 140 (e.g., the second obtaining module 330 illustrated in FIG. 3, the processor 220 illustrated in FIG. 2) may obtain scan data of the object by causing an imaging device to scan the object based on the first position and the one or more second positions.

In some embodiments, the processing device 140 may move the couch (e.g., the couch 114) or the imaging device (e.g., the imaging device 110) until a current relative position of the couch and the imaging device reaches the first position at which the first ROI is in the scanning FOV (e.g., a center of the scanning FOV) of the imaging device. Then the processing device 140 may start the imaging device to scan the object to obtain the scan data of the first ROI. After the scan data of the first ROI is obtained, the processing device 140 may further move the couch or the imaging device until the current relative position of the couch and the imaging device reaches a second position (i.e., moves from the first position to the second position) at which a corresponding second ROI is in the scanning FOV (e.g., a center of the FOV) of the imaging device. Then the processing device 140 may start the imaging device to scan the object to obtain the scan data of the second ROI. After the scan data of the second ROI is obtained, the processing device 140 may further change move the couch or the imaging device until the current relative position of the couch and the imaging device reaches a next second position (i.e., moves from the current second position to a next second position) at which a next corresponding second ROI is in the scanning FOV (e.g., a center of the FOV) of the imaging device, and then obtain the scan data of the next second ROI until the scan data of the last of the one or more second ROIs is obtained.

In the embodiments of the present disclosure, the first position and the one or more second positions may be determined automatically, and the scanning of the object may be automatically performed based on the first position and the one or more second positions, which enables the object to be located in a more accurate scanning position, reduces the workload of the operator, saves human resources, improves the work efficiency, and avoids the low imaging accuracy caused by subjective factors such as inexperience of the operator, thereby reducing the probability that the object needs to be rescanned, reducing the radiation dose received by the patient, and protecting the object's health.

In some embodiments, the processing device 140 may determine a scan plan and cause the imaging device to scan the object based on the scan plan to obtain the scan data. In some embodiments, the processing device 140 may determine the scan plan based on the first position and the one or more second positions. In some embodiments, the scan plan may include a scan range (also referred to as a "scan region") of each of the first ROI and the one or more second ROIs, a scan parameter (e.g., a size) associated with an overlapping region of scanning regions corresponding to two adjacent second ROIs, or the like, or a combination thereof.

In some embodiments, when multiple second ROIs (e.g., lungs, liver, and pelvis) of the object need to be imaged, boundaries of the second ROIs in a scanned image may not be clear enough. Accordingly, in the present disclosure, an overlapping region of scanning regions corresponding two adjacent second ROIs may be determined and added in the scan plan. During the scanning process, the overlapping region may be scanned twice and scan data obtained from the two scans may be superimposed to determine the final scanned image, which can improve the definition of the boundaries of the two adjacent second ROIs. In some embodiments, a size of the overlapping region or a percentage of the overlapping region in any one of the scanning regions corresponding to the two adjacent second ROIs may be larger than a predetermined threshold. For example, the size of the overlapping region may be larger than 600 mm*200 mm, 500 mm*100 mm, 400 mm*100 mm, 400 mm*50 mm etc. As another example, the percentage of the overlapping region in any one of the scanning regions corresponding to the two adjacent second ROIs may be larger than a predetermined percentage (e.g., 5%, 10%, 20%, 25%).

In some embodiments, the processing device 140 may determine the scan plan based on the first position, the one or more second positions, and a parameter associated with a drug (e.g., the tracer species) that is injected into the object. The parameter associated with the drug may include a type of the drug, a metabolism rate of the drug in the object, a flow rate of the drug in the object, or the like, or any combination thereof. Accordingly, the scan plan may further include a moving speed of the object among the first position and the one or more second positions, for example, a moving speed of the object from a first position to a second position, a moving speed of the object from a second position to a next second position, etc. Specifically, the processing device 140 may determine the moving speed of the object among the first position and the one or more second positions based on the metabolism rate and/or the flow rate of the drug in the object. Merely by way of example, the faster the metabolism or the flow rate of the drug is, the faster the moving speed of the object among the first position and the one or more second positions may be.

In some embodiments, the scan plan may further include a scan time. The scan time may include a time when the couch or the imaging device starts to move, a time when the couch or the imaging device reaches the first position or the one or more second positions, a time period (also referred to as a "scan time period") during which the couch or the imaging device stays at the first position or the one or more second positions, or the like, or any combination thereof. In some embodiments, the processing device 140 may determine the scan time based on the first position, the one or more second positions, the moving speed of the object among the first position and the one or more second positions, and the parameter associated with a drug.

In some embodiments, the processing device 140 may show the scan plan to the operator via a display (e.g., the display 240). The operator may manually revise the scan plan (e.g., adjusting the size of the overlapping region) through an input device (e.g., the I/O 260).

Generally, during the scanning, it is necessary to ensure that scan data collection is started at the moment when the drug is injected into the object's body to ensure an accurate scanning process and an accurate scanning result. Accordingly, in some embodiments of the present disclosure, the processing device 140 may start the scan data collection through a preset manner while injecting the drug into the object. The preset manner may include starting the scan data collection through foot pedal sensing, gesture recognition, voice recognition, brain wave recognition, a VR/AR device, a device accessory, or the like, or any combination thereof.

In some embodiments, a foot pedal sensing device may be set up around the imaging device (e.g., the imaging device 110), and the operator may immediately start the scan data collection by touching the foot pedal device.

In some embodiments, a gesture sensing device may be provided around the imaging device. The gesture sensing device may automatically recognize the action of drug injection, and start the scan data collection immediately upon recognizing the action of drug injection.

In some embodiments, a voice recognition device may be provided around the imaging device. The voice recognition device may automatically recognize the operator's voice command to start drug injection, and start the scan data collection immediately upon recognizing the voice command. In addition, the operator may be instructed in drug injection by the voice recognition device. Specifically, the voice recognition device may inform the operator the start time of the scan data collection, and require the operator to perform the drug injection at the time when the scan data collection starts. Merely by way of example, the voice recognition device may inform the operator by means of a countdown reminder for the start of the scan data collection, a prompt sound at the moment when the scan data collection starts, etc.

In some embodiments, a brain wave recognition device may be set on the operator to recognize the brain waves of the operator, and to synchronously start the scan data collection based on the recognized collection instruction issued by the operator's brain.

In some embodiments, an operator of the imaging device and an operator of the drug injection may wear synchronous VR/AR devices. The operator of the imaging device may recognize the injection action through the synchronous VR/AR devices, and start the scan data collection synchronously.

In some embodiments, the drug injection and the scan data collection may be started synchronously through a device accessory (e.g., a button, a key, a switch). For example, a button to start the scan data collection may be provided within an operating range of the operator, and the operator may start the scan data collection through the button while injecting the drug.

In some embodiments, the drug injection and the scan data collection may be started synchronously in other ways. For example, the operator may start the scan data collection by directly touching a touch screen covered by a disposable antibacterial cover.

In the embodiments of the present disclosure, the drug injection and the scan data collection may be started synchronously through multiple preset manners, which avoids or reduces the generation of the invalid scan, thereby avoiding or reducing the errors in subsequent data analysis and processing.

In 440, the processing device 140 (e.g., the second determination module 340 illustrated in FIG. 3, the processor 220 illustrated in FIG. 2) may determine an injection parameter of the drug that is injected into the object based on the scan data.

In some embodiments, the scan data may include a count of pairs of photons detected and/or registered by detectors, position information associated with multiple coincidence events, time information (e.g., a time when a pair of photons reaches the detectors, a time when a pair of photons appears) associated with multiple coincidence events, or the like, or any combination thereof. As described in connection with FIG. 1, a coincidence event may indicate a pair of photons detected by detectors surrounding the object within a preset time window.

In some embodiments, the injection parameter of the drug may include an injection dose of the drug, an injection time of the drug, or the like, or a combination thereof.

In some embodiments, the processing device 140 may determine a count of the coincidence events for the object based on the scan data and further determine the injection dose of the drug based on the count of the coincidence events. More descriptions regarding the determining of the injection dose of the drug may be found elsewhere in the present disclosure, for example, FIG. 8 and the descriptions thereof.

In some embodiments, the processing device 140 may determine a plurality of initial reconstruction images based on at least a portion of the scan data according to a preset temporal frequency and further determine the injection time of the drug based on the plurality of initial reconstruction images. More descriptions regarding the determining of the injection time of the drug may be found elsewhere in the present disclosure, for example, FIG. 9 and the descriptions thereof.

In the embodiments of the present disclosure, the injection time and the injection dose of the drug may be automatically determined, which avoids the operator manually entering the injection time and injection dose, thereby avoiding or reducing manual enter errors, reducing the workload of the operator, improving the accuracy of the determination of the injection time and the injection dose, and improving the efficiency and accuracy of the medical imaging.

In 450, the processing device 140 (e.g., the generation module 350 illustrated in FIG. 3, the processor 220 illustrated in FIG. 2) may generate a target image of the object based on the injection parameter and the scan data of the object.

In some embodiments, the processing device 140 may generate the target image of the object based on the injection parameter, the scan data of the object, and a target model. For example, the processing device 140 may input the injection parameter and the scan data into the target model and determine the target image of the object based on an output of the target model. In some embodiments, the target model may include a reconstruction algorithm, a reconstruction model, a kinetic model, or the like, or any combination thereof. The reconstruction algorithm may include a time of flight (TOF)-based reconstruction algorithm, a deep learning-based reconstruction algorithm, or the like, or any combination thereof. The reconstruction model may include, for example, a trained machine learning model (e.g., a trained neural network model). The kinetic model may indicate a metabolism situation of the drug injected into the object. The kinetic model may include, for example, a compartment model. The compartment model may include a two compartment model, a three compartment model, a four compartment model, or the like, or any combination thereof.

In some embodiments, the processing device 140 may cause a display device (e.g., the display 240) to display a first interface. The first interface may include a plurality of preset models (e.g., a plurality of preset kinetic models) each of which indicates a conversion relationship among parameters of the preset model. The operator may manually select a preset model from the plurality of preset models through an input device (e.g., the I/O 260). In response to the selection, a trigger instruction is generated. In response to the trigger instruction, the processing device 140 may assign the preset model selected by the operator as the target model and cause the display device to display a second interface based on the target model. The second interface may include at least one parameter image each of which is related to a parameter of the target model. In some embodiments, the second interface may also include the target image of the object generated based on the target model. In some embodiments, the second interface may also include other related images of the target image, for example, the initial image of the object, a fused image of the target image and another image of the object, etc. More descriptions regarding the first interface and the second interface may be found elsewhere in the present disclosure, for example, FIGS. 10-15 and the descriptions thereof.

In the embodiments of the present disclosure, the conversion relationship among parameters of the preset model and the parameter images related to the parameters of the preset model are displayed in the form of images instead of form of texts, which can be intuitively understood by operators and is more widely applicable.

It should be noted that the above description of the process 400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 5:
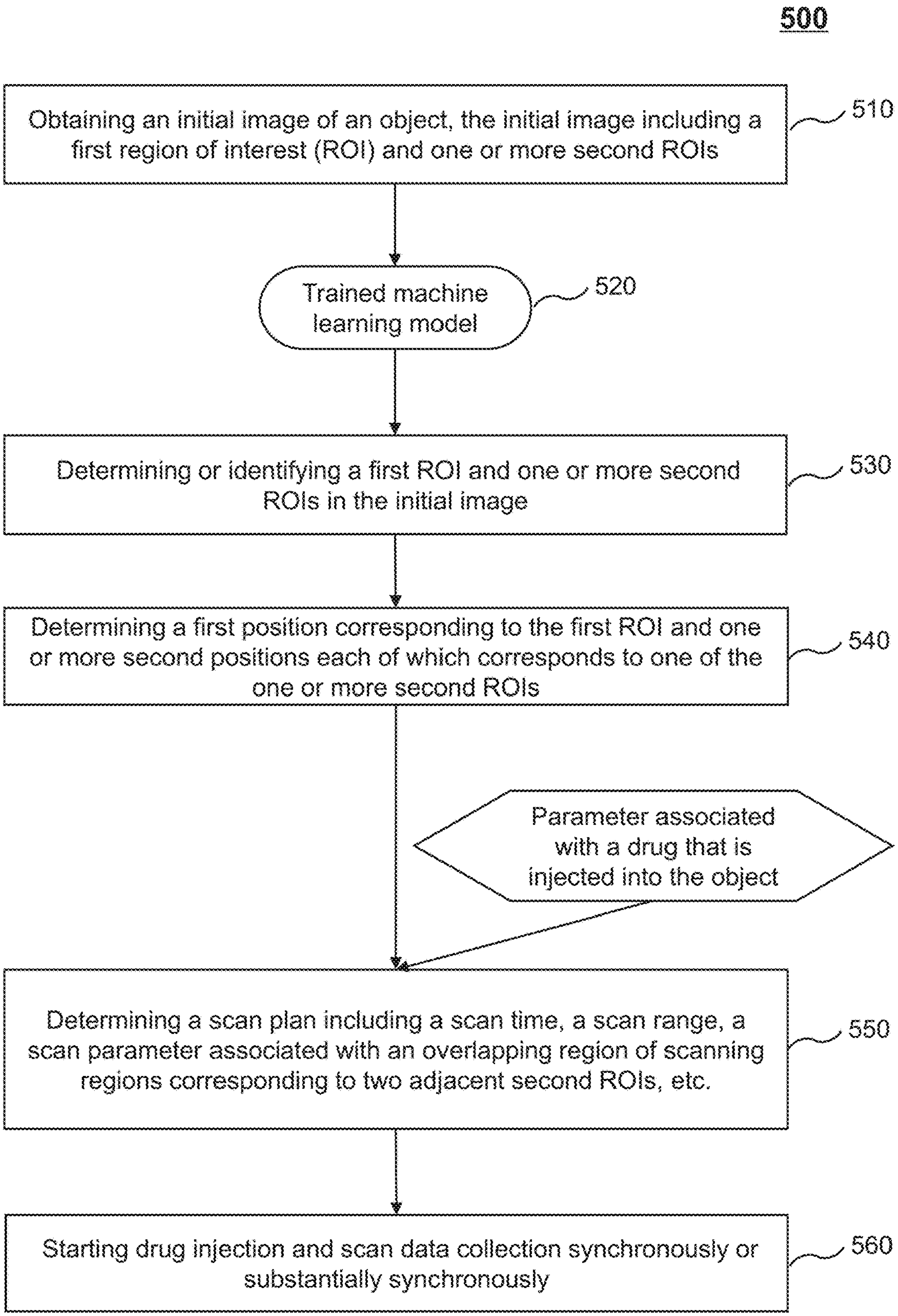
FIG. 5 is a flowchart illustrating an exemplary process for medical imaging according to some embodiments of the present disclosure.

FIG. 5 is a flowchart illustrating an exemplary process for medical imaging according to some embodiments of the present disclosure. In some embodiments, process 500 may be executed by the medical imaging system 100. For example, the process 500 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 510, the processing device 140 (e.g., the first obtaining module 310 illustrated in FIG. 3, the processor 220 illustrated in FIG. 2) may obtain an initial image (e.g., a scout view) of an object (e.g., a human body). The obtaining of the initial image may be performed in a similar manner as described in connection with operation 410, and the descriptions thereof are not repeated here.

In 520, the processing device 140 (e.g., the first determination module 320 illustrated in FIG. 3, the processor 220 illustrated in FIG. 2) may input the initial image into a trained machine learning model.

Figure 6A:
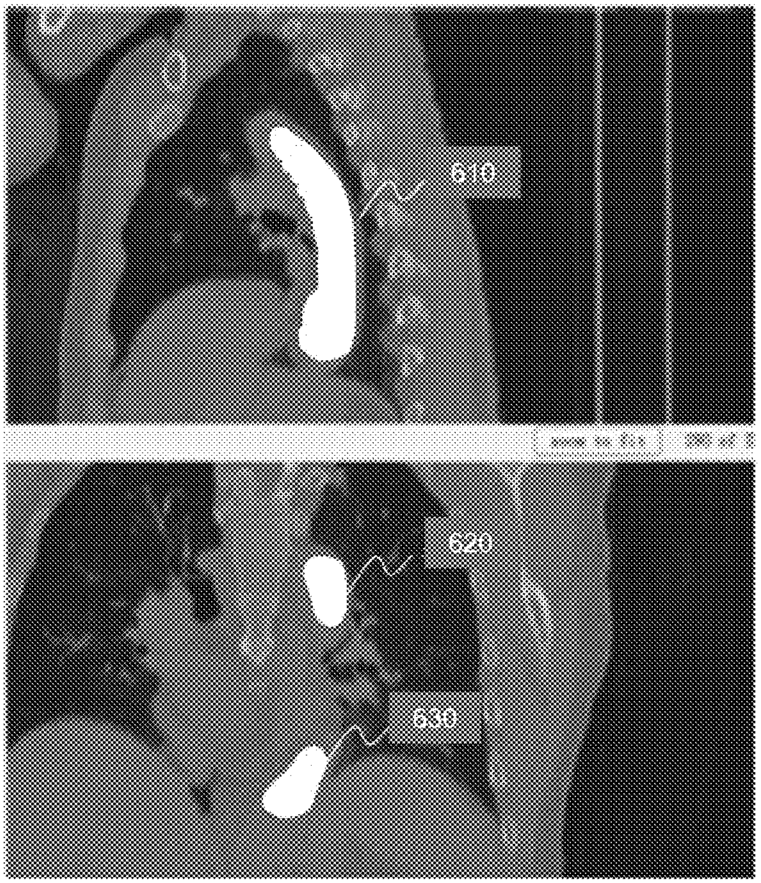
FIG. 6A and FIG. 6B are schematic diagrams illustrating exemplary first ROIs and an exemplary second ROI according to some embodiments of the present disclosure.
Figure 6B:
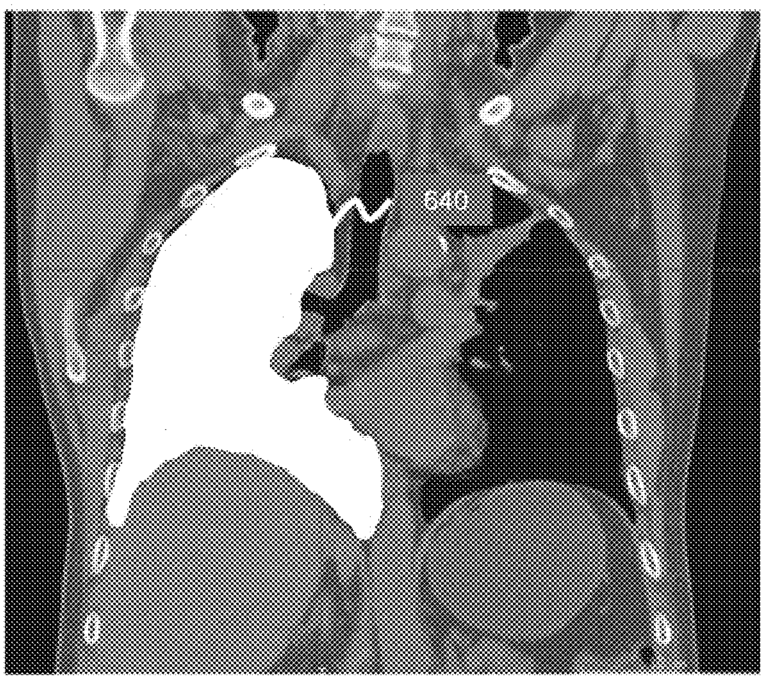

In 530, the processing device 140 (e.g., the first determination module 320 illustrated in FIG. 3, the processor 220 illustrated in FIG. 2) may determine or identify a first ROI (e.g., aortic blood pools) and one or more second ROIs (e.g., lungs, liver, pelvis) in the initial image based on an output of the trained machine learning model. For example, FIG. 6A and FIG. 6B are schematic diagrams illustrating exemplary first ROIs and an exemplary second ROI according to some embodiments of the present disclosure. As illustrated in FIGS. 6A, 610, 620, and 630 refer to aortic blood pools (first ROIs) in the initial image. As illustrated in FIG. 6B, 640 refers to a lung (second ROI) in the initial image.

In 540, the processing device 140 (e.g., the first determination module 320 illustrated in FIG. 3, the processor 220 illustrated in FIG. 2) may determine a first position corresponding to the first ROI and one or more second positions each of which corresponds to one of the one or more second ROIs based on the first ROI and the one or more second ROI. More descriptions regarding the determining of the first position and the one or more second positions may be found elsewhere in the present disclosure, for example, operation 420 and the descriptions thereof.

In 550, the processing device 140 (e.g., the first determination module 320 illustrated in FIG. 3, the processor 220 illustrated in FIG. 2) may determine a scan plan based on the first position, the one or more second positions, and a parameter associated with a drug (e.g., the tracer species) that is injected into the object. In some embodiments, the scan plan at least includes a scan time, a scan range, a scan parameter associated with an overlapping region of scanning regions corresponding to two adjacent second ROIs, etc. More descriptions regarding the determining of the scan plan may be found elsewhere in the present disclosure, for example, operation 430 and the descriptions thereof.

In 560, the processing device 140 (e.g., the first determination module 320 illustrated in FIG. 3, the processor 220 illustrated in FIG. 2) may start drug injection and scan data collection synchronously or substantially synchronously. More descriptions regarding the start of the drug injection and the scan data collection may be found elsewhere in the present disclosure, for example, operation 430 and the descriptions thereof.

Figure 7A:
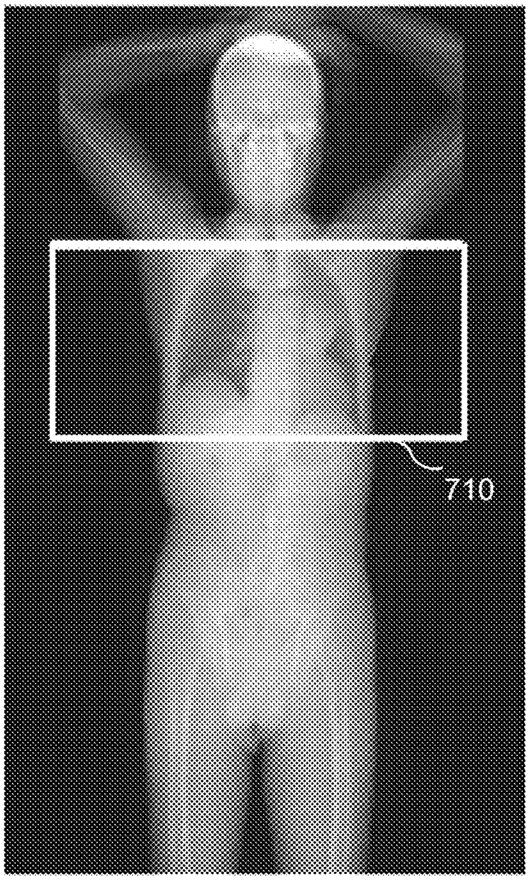
FIG. 7A and FIG. 7B are schematic diagrams illustrating an exemplary scanning process of a first ROI and three second ROIs according to some embodiments of the present disclosure.
Figure 7B:
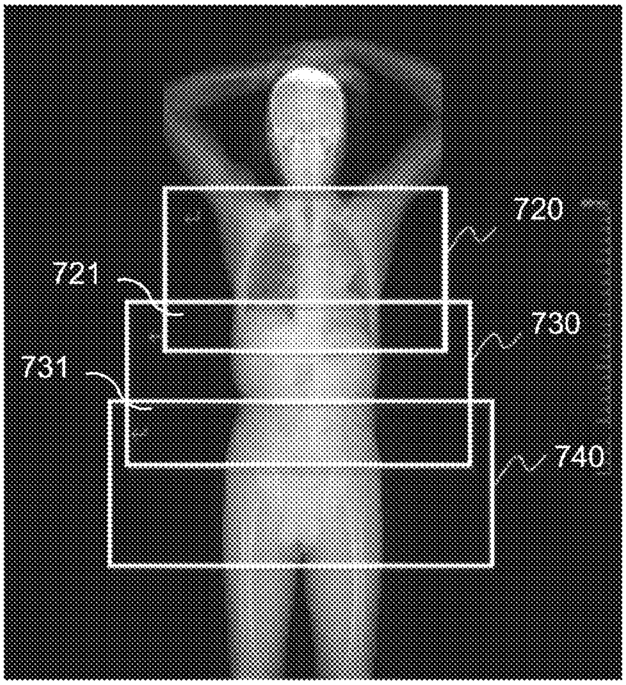

FIG. 7A and FIG. 7B are schematic diagrams illustrating an exemplary scanning process of a first ROI and three second ROIs according to some embodiments of the present disclosure. As illustrated in FIG. 7A and FIG. 7B, the first ROI includes aortic blood pools; the three second ROIs include lungs, liver, and pelvis. Specifically, the processing device 140 may move the couch or the imaging device until a current relative position of the couch and the imaging device reaches a first position corresponding to the first ROI (i.e., aortic blood pools). As illustrated in FIG. 7A, when the current relative position of the couch and the imaging device reaches the first position, the first ROI (i.e., aortic blood pools) is within a FOV 710 (e.g., a center of the FOV 710) of the imaging device. Then, at a scan time of the first ROI (i.e., aortic blood pools) in a scan plan of the object, the processing device 140 may start the imaging device to scan the object to obtain the scan data of the first ROI (i.e., aortic blood pools).

After the scan data of the first ROI (i.e., aortic blood pools) is obtained, the processing device 140 may further move the couch or the imaging device until the current relative position of the couch and the imaging device reaches a second position corresponding to lungs. As illustrated in FIG. 7B, when the current relative position of the couch and the imaging device reaches the second position, the lungs are within a FOV 720 (e.g., a center of the FOV 720) of the imaging device. Then, at a scan time of the lungs in the scan plan of the object, the processing device 140 may start the imaging device to scan the object to obtain the scan data of the lungs.

After the scan data of the lungs is obtained, the processing device 140 may further move the couch or the imaging device until the current relative position of the couch and the imaging device reaches a next second position corresponding to the liver. As illustrated in FIG. 7B, when the current relative position of the couch and the imaging device reaches the next second position, the liver is in a FOV 730 (e.g., a center of the FOV 730) of the imaging device. Then, at a scan time of the liver in the scan plan of the object, the processing device 140 may start the imaging device to scan the object to obtain the scan data of the liver.

After the scan data of the liver is obtained, the processing device 140 may further move the couch or the imaging device until the current relative position of the couch and the imaging device reaches a last second position corresponding to the pelvis. As illustrated in FIG. 7B, when the current relative position of the couch and the imaging device reaches the last second position, the pelvis is in a FOV 740 (e.g., a center of the FOV 740) of the imaging device. Then, at a scan time of the pelvis in the scan plan of the object, the processing device 140 may start the imaging device to scan the object to obtain the scan data of the pelvis.

As illustrated in FIG. 7B, the FOV 720 and the FOV 730 have an overlapping region 721. The overlapping region 721 is scanned when the lungs are scanned, and is scanned again when the liver is scanned. Scan data obtained from the two scans of the overlapping region 721 may be superimposed when the scan data is processed, which may improve the definition of the boundary of each of the lungs and the liver in the obtained image of the object. Similarly, an overlapping region 731 of the FOV 730 and the FOV 740 is also scanned twice, which may improve the definition of the boundary of each of the liver and the pelvis in the obtained image of the object.

It should be noted that the above description of the process 400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 8:
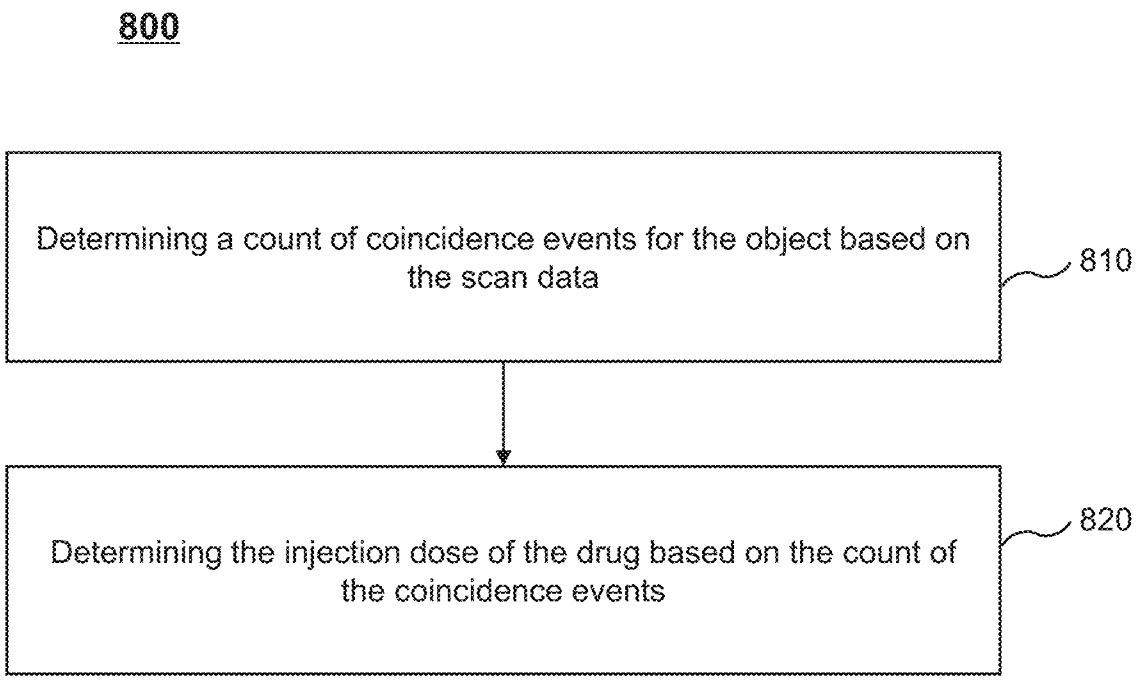
FIG. 8 is a flowchart illustrating an exemplary process for determining an injection dose of a drug according to some embodiments of the present disclosure.

FIG. 8 is a flowchart illustrating an exemplary process for determining an injection dose of a drug according to some embodiments of the present disclosure. In some embodiments, process 800 may be executed by the medical imaging system 100. For example, the process 800 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, one or more operations of the process 800 may be performed to achieve at least part of operation 440 as described in connection with FIG. 4.

In 810, the processing device 140 (e.g., the second determination module 340 illustrated in FIG. 3, the processor 220 illustrated in FIG. 2) may determine a count of coincidence events for the object based on the scan data. In some embodiments, as described in connection with above, a coincidence event indicating a pair of photons detected by detectors surrounding the object within a preset time window.

In some embodiments, as described in connection with operation 410, an ROI may be selected manually or by the processing device 140, and a count of coincidence events associated with selected ROI may be determined based on scan data of the selected ROI. In some embodiments, the selected ROI may include the whole object, that is, the whole object needs to be within the FOV of the imaging device. In some embodiments, the scan data may include a count of pairs of photons detected and/or registered by detectors, position information associated with multiple coincidence events, time information (e.g., a time when a pair of photons reaches the detectors, a time when a pair of photons appears) associated with multiple coincidence events, or the like, or any combination thereof. In some embodiments, the scan data may be list mode data.

In some embodiments, the processing device 140 may determine the count of the coincidence events by correcting an initial count of the coincidence events. For example, the processing device 140 may correct the initial count of the coincidence events based on a decay correction function to obtain a corrected count of the coincidence events, and designated the corrected count of the coincidence events as the count of the coincidence events. In some embodiments, the processing device 140 may determine the count of the coincidence events according to Equation (1) as below:

$$C_{correct}=C_{measuree}e^{\lambda t}, \tag{1}$$

where $C_{correct}$ denotes the corrected count of the coincidence events at a moment t later than or equal to an injection time of the drug, $C_{measure}$ denotes the initial count of the coincidence events at the moment t, e denotes the natural constant, and λ denotes a decay constant.

In 820, the processing device 140 (e.g., the second determination module 340 illustrated in FIG. 3, the processor 220 illustrated in FIG. 2) may determine the injection dose of the drug based on the count of the coincidence events.

In some embodiments, the processing device 140 may obtain a relationship between the count of the coincidence events and the injection dose of the drug. In some embodiments, the relationship may be a proportional relationship (e.g., a linear proportional relationship or a nonlinear proportional relationship). For example, the greater the count of the coincidence events is, the greater the injection dose of the drug may be. Further, the processing device 140 may determine the injection dose of the drug according to the count of the coincidence events and the relationship between the count of the coincidence events and the injection dose of the drug.

In some embodiments, the processing device 140 may obtain multiple reference counts of coincidence events and reference injection doses of the drug during multiple reference medical imaging processes (e.g., historical medical imaging processes). Further, the processing device 140 may determine the relationship between the count of the coincidence events and the injection dose of the drug based on the multiple reference counts of coincidence events and the reference injection doses of the drug. For example, the processing device 140 may determine the relationship between the count of the coincidence events and the injection dose of the drug based on the multiple reference counts of coincidence events and the reference injection doses of the drug according to a preset algorithm (e.g., a linear fitting algorithm).

In some embodiments, the relationship between the count of the coincidence events and the injection dose of the drug may be stored in a storage device (e.g., the storage device 150, the storage 230, an external storage device) or an external system. The processing device 140 may obtain the relationship between the count of the coincidence events and the injection dose of the drug from the storage device or the external system directly or via a network (e.g., the network 120).

Figure 9:
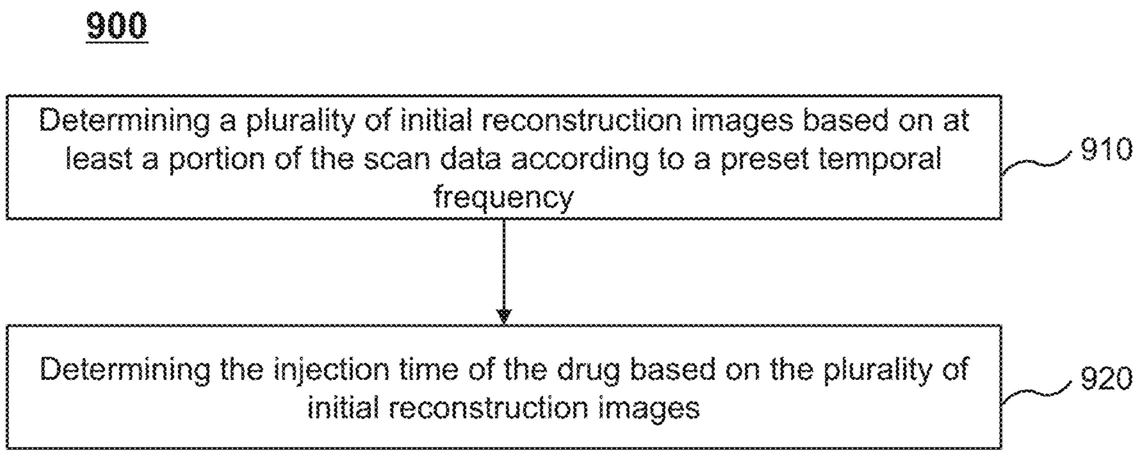
FIG. 9 is a flowchart illustrating an exemplary process for determining an injection time of a drug according to some embodiments of the present disclosure.

FIG. 9 is a flowchart illustrating an exemplary process for determining an injection time of a drug according to some embodiments of the present disclosure. In some embodiments, process 900 may be executed by the medical imaging system 100. For example, the process 900 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting. In some embodiments, one or more operations of the process 900 may be performed to achieve at least part of operation 440 as described in connection with FIG. 4.

In 910, the processing device 140 (e.g., the second determination module 340 illustrated in FIG. 3, the processor 220 illustrated in FIG. 2) may determine a plurality of initial reconstruction images based on at least a portion of the scan data according to a preset temporal frequency.

The preset temporal frequency may refer to a reconstruction frequency (e.g., 1 s/frame) of the plurality of initial reconstruction images or a time interval (e.g., 1 s) between adjacent initial reconstruction images. In some embodiments, the preset temporal frequency may be set manually by a user (e.g., an engineer), a default setting of the medical imaging system 100, or determined by the processing device 140 according to an actual need. For example, the preset temporal frequency may be 1 s/frame, 0.8 s/frame, 0.5 s/frame, 0.1 s/frame, 1 s, 0.8 s, 0.5 s, 0.1 s, etc. In some embodiments, the preset temporal frequency may be determined according to an accuracy requirement of the injection time of the drug. The higher the accuracy requirement of the injection time is, the smaller the preset temporal frequency may be; the lower the accuracy requirement of the injection time is, the greater the preset temporal frequency may be.

In some embodiments, the processing device 140 may determine the plurality of initial reconstruction images using a reconstruction algorithm. Exemplary reconstruction algorithms may include a time of flight (TOF)-based reconstruction algorithm, a deep learning-based reconstruction algorithm, or the like, or any combination thereof.

In 920, the processing device 140 (e.g., the second determination module 340 illustrated in FIG. 3, the processor 220 illustrated in FIG. 2) may determine the injection time of the drug based on the plurality of initial reconstruction images.

As described elsewhere in the present disclosure, the injection of the drug and the scan data collection are executed synchronously or substantially synchronously. Accordingly, the scan data (or the initial reconstruction images determined based on the scan data) includes information corresponding a start time (i.e., an injection time) of the injection of the drug. In some embodiments, the scanning FOV of the imaging device may include the whole object. In this situation, the scan data can be directly used to determine the initial reconstruction images and further used to estimate the injection time of the drug. In some embodiments, the scanning FOV of the imaging device may not include the whole object. In this situation, scan data at least including scan data of a position on the object where the drug is injected into may be used to determine the initial reconstruction images and further used to estimate the injection time of the drug, that is, it should be ensured that the scan data used to determine the initial reconstruction images and further used to estimate the injection time of the drug includes information corresponding the start time of the injection of the drug.

In some embodiments, since pixel values corresponding to the drug and pixel values corresponding to normal organs or tissues in an initial reconstruction image are different, the pixel values associated with a target region can be used to identify whether the drug occurs in the or the target region or not. The target region refers to a region that includes the position on the object where the drug is injected into. In some embodiments, the first ROI may include the target region. Accordingly, for each of the plurality of initial reconstruction images, the processing device 140 may determine pixel values associated with the target region. For example, the processing device 140 may directly determine pixel values corresponding to the target region. Further, the processing device 140 may determine a target reconstruction image from the plurality of initial reconstruction images based on the pixel values corresponding to the plurality of initial reconstruction images respectively. The target reconstruction image may correspond to target pixel values indicating that the target reconstruction image is the first image, among the plurality of initial reconstruction images, that indicates an occurrence of the drug and accordingly indicates the injection time of the drug.

In some embodiments, the processing device 140 may determine the target reconstruction image using a drug detection model based on the initial reconstruction images. The drug detection model may be a trained model (e.g., a machine learning model) used for drug detection. Specifically, the processing device 140 may input the initial reconstruction images and acquisition times associated with the initial reconstruction images into the drug detection model and the drug detection model may output the target reconstruction image. The acquisition time associated with the initial reconstruction image may refer to a collection time of the scan data for generating the initial reconstruction image. In some embodiments, the acquisition time associated with the initial reconstruction image may be any time point from a starting time to an ending time of the collection of the scan data for generating the initial reconstruction image. For example, the acquisition time associated with the initial reconstruction image may be the starting time or the ending time of the collection of the scan data for generating the initial reconstruction image. In some embodiments, the processing device 140 may input each of the initial reconstruction images into the drug detection model and the drug detection model may output whether the initial reconstruction image includes the drug. The processing device 140 may include determine an initial reconstruction images including the drug with an earliest acquisition time from the initial reconstruction images including the drug as the target reconstruction image. Exemplary drug detection models may include a deep belief network (DBN) model, a CNN model, an RNN model, a generative adversarial network (GAN) model, or the like, or any combination thereof.

In some embodiments, the processing device 140 may obtain the drug detection model from one or more components (e.g., the storage device 150, the storage 230) of the medical imaging system 100 or an external source via a network (e.g., the network 120). For example, the drug detection model may be previously trained by a computing device (e.g., the processing device 140), and stored in a storage device (e.g., the storage device 150, the storage 220) of the medical imaging system 100. The processing device 140 may access the storage device and retrieve the drug detection model. In some embodiments, the drug detection model may be generated according to a machine learning algorithm.

Merely by way of example, the drug detection model may be trained according to a supervised learning algorithm by the processing device 140 or another computing device (e.g., a computing device of a vendor of the drug detection model). The processing device 140 may obtain one or more training samples and a preliminary model. Each training sample may include a plurality of sample images, acquisition times associated with the plurality of sample images, and a ground truth reference image. The processing device 140 may obtain the drug detection model by training the preliminary model based on the one or more training samples.

Figure 10:
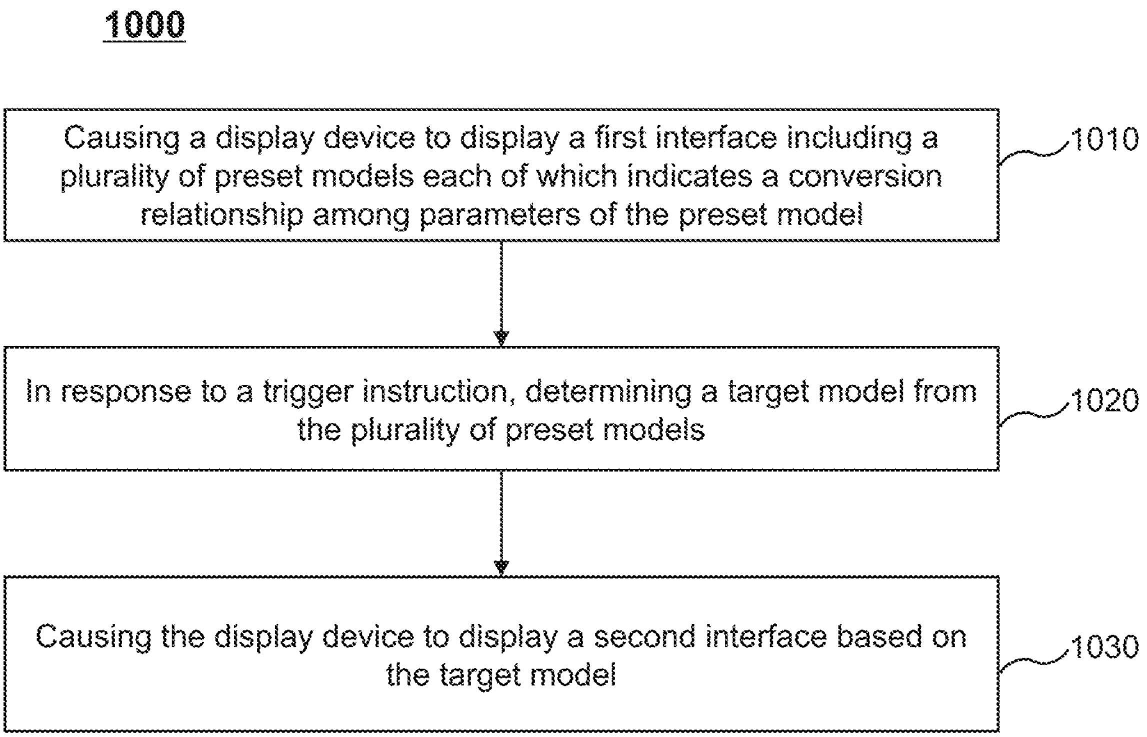
FIG. 10 is a flowchart illustrating an exemplary process for model visualization for generating a target image of an object according to some embodiments of the present disclosure.

FIG. 10 is a flowchart illustrating an exemplary process for model visualization for generating a target image of an object according to some embodiments of the present disclosure. In some embodiments, process 1000 may be executed by the medical imaging system 100. For example, the process 1000 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 1000. The operations of the illustrated process presented below are intended to be illustrative. In some embodiments, the process 1000 may be accomplished with one or more additional operations not described and/or without one or more of the operations discussed. Additionally, the order of the operations of process 1000 illustrated in FIG. 10 and described below is not intended to be limiting. In some embodiments, one or more operations of the process 1000 may be performed to achieve at least part of operation 450 as described in connection with FIG. 4.

In 1010, the processing device 140 (e.g., the second determination module 340 illustrated in FIG. 3, the processor 220 illustrated in FIG. 2) may cause a display device (e.g., the display 240) to display a first interface (e.g., an interface 1200) including a plurality of preset models each of which indicates a conversion relationship among parameters of the preset model.

In some embodiments, the conversion relationship among parameters of the preset model may be represented in various forms, for example, image, formula, text, etc.

In some embodiments, the preset model may include a kinetic model (e.g., a pharmacokinetic model). The pharmacokinetic model may indicate a metabolism situation of a drug injected into the object. Pharmacokinetics may be used to quantitatively study an absorption, a distribution, a metabolism, and/or an excretion of a drug in an object, and describe the drug concentration changes over time using mathematical principles or methods. The pharmacokinetic model may be used to quantitatively study kinetic processes of the drug in the object. Accordingly, the parameters of the pharmacokinetic model may reflect the dynamic change of the drug in the object and may quantitatively describe dynamic characteristics of the drug in the object over time. Exemplary parameters of the pharmacokinetic model may include a concentration of the drug in plasmas or tissues of the object, transportation rates (e.g., denoted as "K" (e.g., K1, K2, K3, K4, Ki illustrated in FIG. 12)) of the drug among plasmas and tissues of the object, a ratio of the drug concentration in tissue to the drug concentration in plasma after the drug flow reaches equilibrium (e.g., denoted as VT, VND, BPND illustrated in FIG. 12).

In some embodiments, the preset model may include a compartment model, an elimination kinetic model, or the like, or any combination thereof. The compartment model refers to a model that divides an object into a plurality of compartments according to dynamic characteristics of a drug, which can simplify the complex biological system, so that the dynamic process of the drug in the object can be quantitatively analyzed. In some embodiments, the compartment model may include a two-compartment model, a three-compartment model, or a four-compartment model, or the like, or any combination thereof.

Figure 11A:
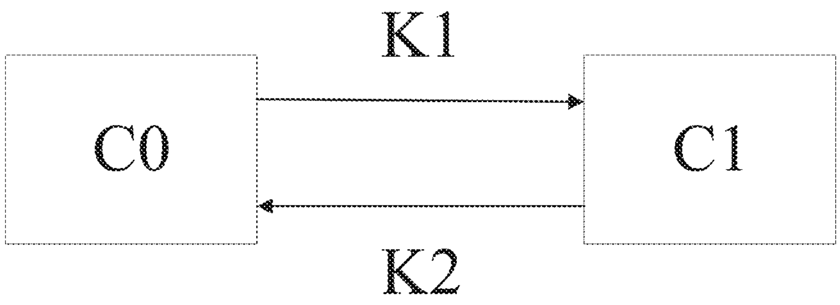
FIG. 11A is a schematic diagram illustrating an exemplary two-compartment model according to some embodiments of the present disclosure.

The two-compartment model may include a central compartment and a peripheral compartment. The central compartment may include portions of the object in which the drug can be equilibrated shortly after the drug is injected into the object. For example, the central compartment may include the blood and tissues that can be instantly equilibrated with the blood, such as the kidneys, the brain, the heart, the liver, etc. The peripheral compartment may include tissues with relatively low blood flow, such as fat, muscle, bone, cartilage, etc. After the drug is injected into the object, the drug may be immediately distributed to the central compartment and then slowly to the peripheral compartment. Exemplary parameters of the two-compartment model may include a transportation rate of the drug, a conversion rate of the drug, etc. For example, FIG. 11A is a schematic diagram illustrating an exemplary two-compartment model according to some embodiments of the present disclosure. As shown in FIG. 11A, the two-compartment model 1100A may include a central compartment (e.g., a plasma compartment C0) and a peripheral compartment (e.g., a tissue compartment C1). The parameters of the two-compartment model may include a parameter K1 describing a transport (e.g., a transport rate) of the drug from the plasma compartment C0 to the tissue compartment C1 and a parameter K2 describing a transport (e.g., a transport rate) of the drug from the tissue compartment C1 to the plasma compartment C0.

Figure 11B:
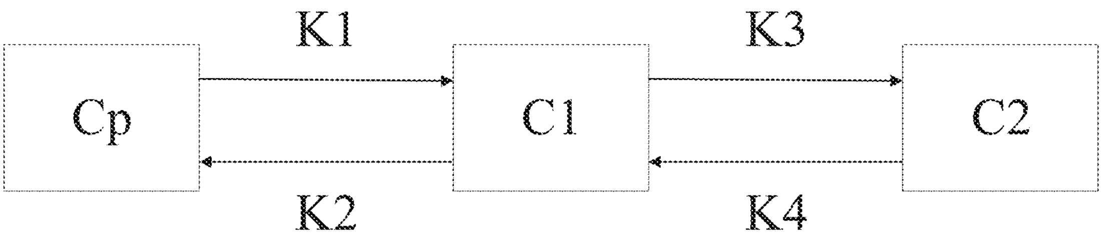
FIG. 11B is a schematic diagram illustrating an exemplary three-compartment model according to some embodiments of the present disclosure.

The three-compartment model may include a central compartment, a first peripheral compartment, and a second peripheral compartment. The central compartment may include a region where the drug reaches fast. The first peripheral compartment may include a region (e.g., tissues or organs with relatively poor blood perfusion) where the drug reaches relatively slowly. The second peripheral compartment may include a region (e.g., tissues or organs with poorer blood perfusion than the first peripheral compartment) where the drug reaches more slowly, such as bone marrow, fat, tissues that are strongly bound to the drug, etc. After the drug is injected into the object, the drug may be immediately distributed to the central compartment, then into the first peripheral compartment at a rate slower than that of the central compartment, and further into the second peripheral compartment at a rate slower than that of the first peripheral compartment. For example, FIG. 11B is a schematic diagram illustrating an exemplary three-compartment model according to some embodiments of the present disclosure. As shown in FIG. 11B, the three-compartment model 1100B may include a central compartment (e.g., a plasma compartment Cp), a first peripheral compartment (e.g., a first tissue compartment C1), and a second peripheral compartment (e.g., a second tissue compartment C2). The parameters of the three-compartment model 11006 may include a parameter K1 describing a transport (e.g., a transport rate) of the drug from the plasma compartment C0 to the first tissue compartment C1, a parameter K2 describing a transport (e.g., a transport rate) of the drug from the first tissue compartment C1 to the plasma compartment C0, a parameter K3 describing a transport (e.g., a transport rate) of the drug from the first tissue compartment C1 to the second tissue compartment C2, and a parameter K4 describing a transport (e.g., a transport rate) of the drug from the second tissue compartment C2 to the first tissue compartment C1.

Figure 11C:
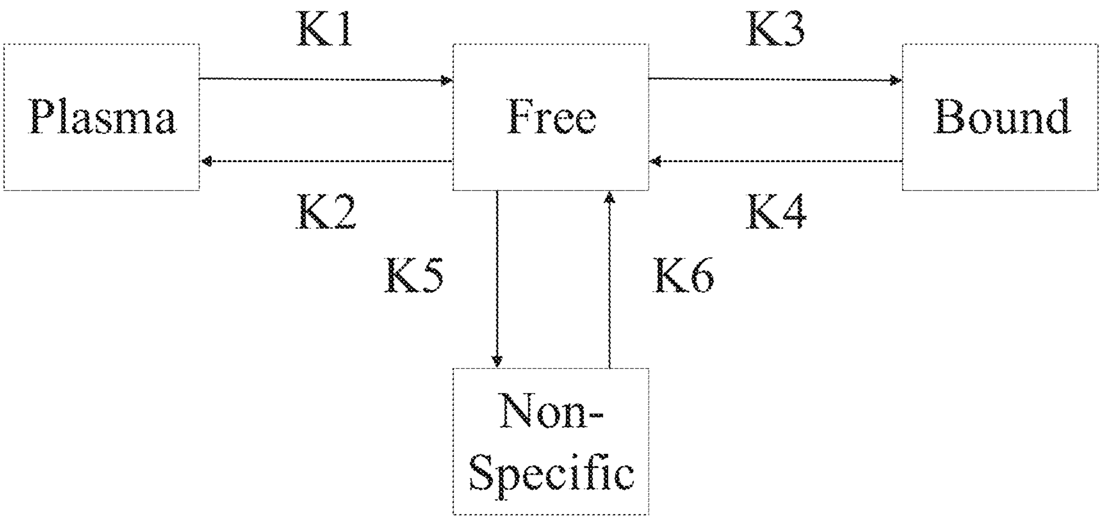
FIG. 11C is a schematic diagram illustrating an exemplary four-compartment model according to some embodiments of the present disclosure.

The four-compartment model may include a central compartment (also referred to as a "plasma compartment"), a first peripheral compartment (also referred to as a "free tissue compartment"), a second peripheral compartment (also referred to as a "non-specific bound compartment"), and a third peripheral compartment (also referred to as a "bound tissue compartment"). The free tissue compartment may include tissues or organs where the drug is free and is not bound to receptors. The non-specific bound compartment may include tissues or organs where the drug is bound to the tissues or organs and is not bound to receptors. The bound tissue compartment may include tissues or organs where the drug is bound to receptors. For example, FIG. 11C is a schematic diagram illustrating an exemplary four-compartment model according to some embodiments of the present disclosure. As shown in FIG. 11C, the fourth compartment model 1100C may include a central compartment (e.g., a plasma compartment Plasma), a first peripheral compartment (e.g., a free tissue compartment Free), a second peripheral compartment (e.g., a non-specific combination compartment Non-Specific), and a third peripheral compartment (e.g., a bound tissue compartment Bound). The parameters of the four-compartment model 1100C may include parameters K1-K6. The parameter K1 may describe a transport (e.g., a transport rate) of the drug from the plasma compartment Plasma to the free tissue compartment Free. The parameter K2 may describe a transport (e.g., a transport rate) of the drug from the free tissue compartment Free to the plasma compartment Plasma. The parameter K3 may describe a transport (e.g., a transport rate) of the drug from the free tissue compartment Free to the bound tissue compartment Bound. The parameter K4 may describe a transport (e.g., a transport rate) of the drug from the bound tissue compartment Bound to the free tissue compartment Free. The parameter K5 may describe a transport (e.g., a transport rate) of the drug from the free tissue compartment Free to the non-specific combination compartment Non-Specific. The parameter K6 may describe a transport (e.g., a transport rate) of the drug from the non-specific combination compartment Non-Specific to the free tissue compartment Free.

In some embodiments, the plurality of preset models may be displayed at suitable positions on the first interface, for example, the top, the bottom, the left, the right, etc. of the first interface. In some embodiments, the plurality of preset models may be displayed via various manners. For example, the plurality of preset models may be displayed on the first interface at the same time. As another example, the plurality of preset models may be displayed in sequence according to a user instruction.

Figure 12:
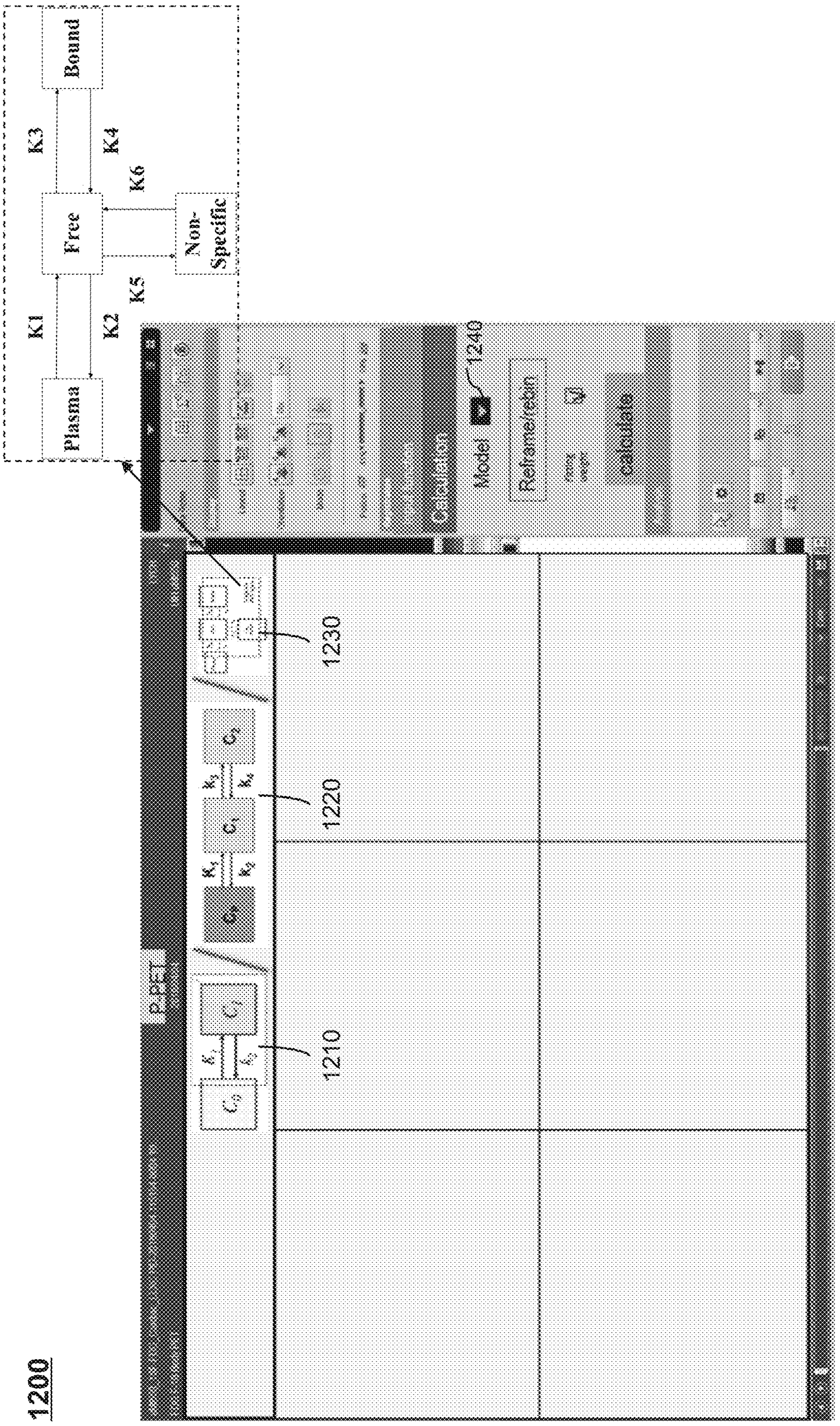
FIG. 12 is a schematic diagram illustrating an exemplary first interface according to some embodiments of the present disclosure.

Merely by way of example, FIG. 12 is a schematic diagram illustrating an exemplary first interface according to some embodiments of the present disclosure. As shown in FIG. 12, a two-compartment model 1210, a three-compartment model 1220, and a four-compartment model 1230 may be displayed on the top of the first interface 1200. Each of the two-compartment model 1210, the three-compartment model 1220, and the four-compartment model 1230 may indicate a conversion relationship among parameters of the model. The conversion relationship among parameters of each model may be represented in the form of an image.

In 1020, in response to a trigger instruction, the processing device 140 (e.g., the second determination module 340 illustrated in FIG. 3, the processor 220 illustrated in FIG. 2) may determine a target model from the plurality of preset models.

The trigger instruction may be an instruction generated by a user selecting the target model through the first interface. For example, the user may click on images corresponding to the preset models to select any one of the preset models.

As shown in FIG. 12, a folding option 1240 of the preset models may be set on the right of the first interface 1200. The user may click the folding option 1240 so that the display device may pop up multiple options (e.g., a drop-down list, thumbnails) each of which may correspond to a preset model, and the user may select one from the multiple options to determine the target model.

In 1030, the processing device 140 (e.g., the second determination module 340 illustrated in FIG. 3, the processor 220 illustrated in FIG. 2) may cause the display device to display a second interface based on the target model.

Figure 13:
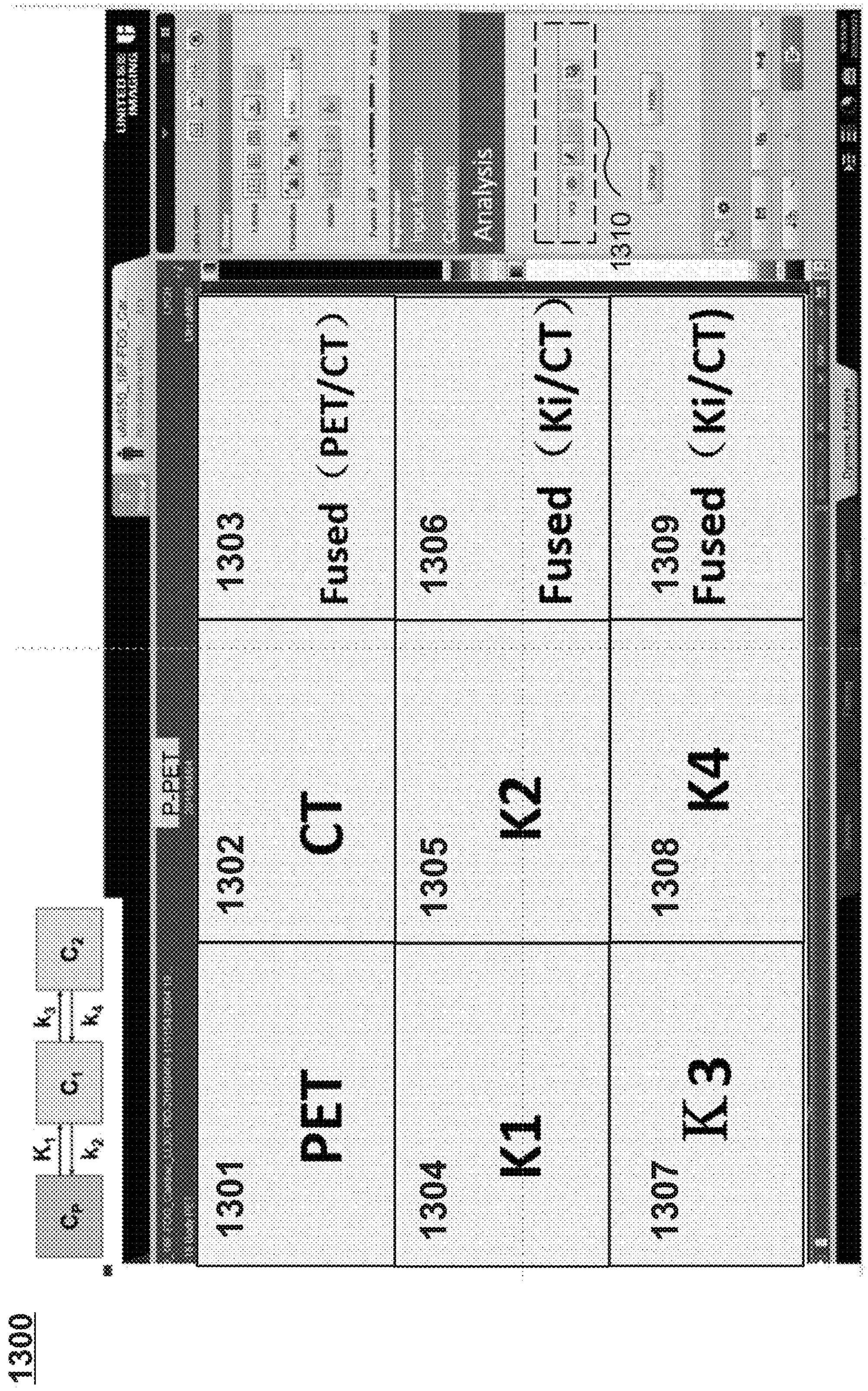
FIG. 13 is a schematic diagram illustrating an exemplary second interface corresponding to a three-compartment model according to some embodiments of the present disclosure.

In some embodiments, the second interface may include a plurality of regions used to display relevant information corresponding to the parameters of the target model. For example, FIG. 13 is a schematic diagram illustrating an exemplary second interface corresponding to a three-compartment model according to some embodiments of the present disclosure. As shown in FIG. 13, the second interface 1300 includes regions 1304, 1305, 1307, and 1308 used to display relevant information corresponding to the four parameters K1, K2, K3, and K4 of the three-compartment model. In some embodiments, the relevant information corresponding to the parameters of the target model may include at least one parameter image each of which is related to a parameter of the target model. Take a specific parameter of the target model as an example, the at least one parameter image may be an image reflecting an evaluation of the physiology (functionality) and/or anatomy (structure) of organs and/or tissues in the object under the specific parameter. In some embodiments, the at least one parameter image may include one or more static images corresponding to one or more time points. Alternatively, the at least one parameter image may include a dynamic parametric image, such as a graphic interchange format (GIF) image that reflects the change of the parameters with respect to time.

In some embodiments, the second interface may also include other regions used to display reference information associated with the target model. For example, as illustrated in FIG. 13, the second interface 1300 also includes regions 1301-1303, 1306, and 1309 used to display reference images (e.g., a PET image, a CT image, a fused image).

In some embodiments, a layout of the regions in the second interface may be set manually by a user (e.g., an engineer) according to an actual need or a default setting of the medical imaging system 100. The layouts of the regions in the second interface corresponding to different preset models may be the same or different.

In some embodiments, as described in connection with operation 410, an ROI (e.g., a second ROI) may be selected manually (e.g., through a tool area 1310 illustrated in FIG. 13) or by the processing device 140, and the processing device 140 may cause the display device to display the relevant information corresponding to the parameters of the target model and/or the reference information associated with the target model in the second interface based on the selected ROI. In some embodiments, the selected ROI may be displayed in the reference information associated with the target model and/or the relevant information corresponding to the parameters of the target model according to an actual need or a default setting of the medical imaging system 100. For example, the selected ROI may be displayed in reference images (e.g., a PET image, a CT image, a fused image) according to a default setting of the medical imaging system 100. As another example, the selected ROI may be displayed in at least one parameter image according to an actual need.

Figure 14:
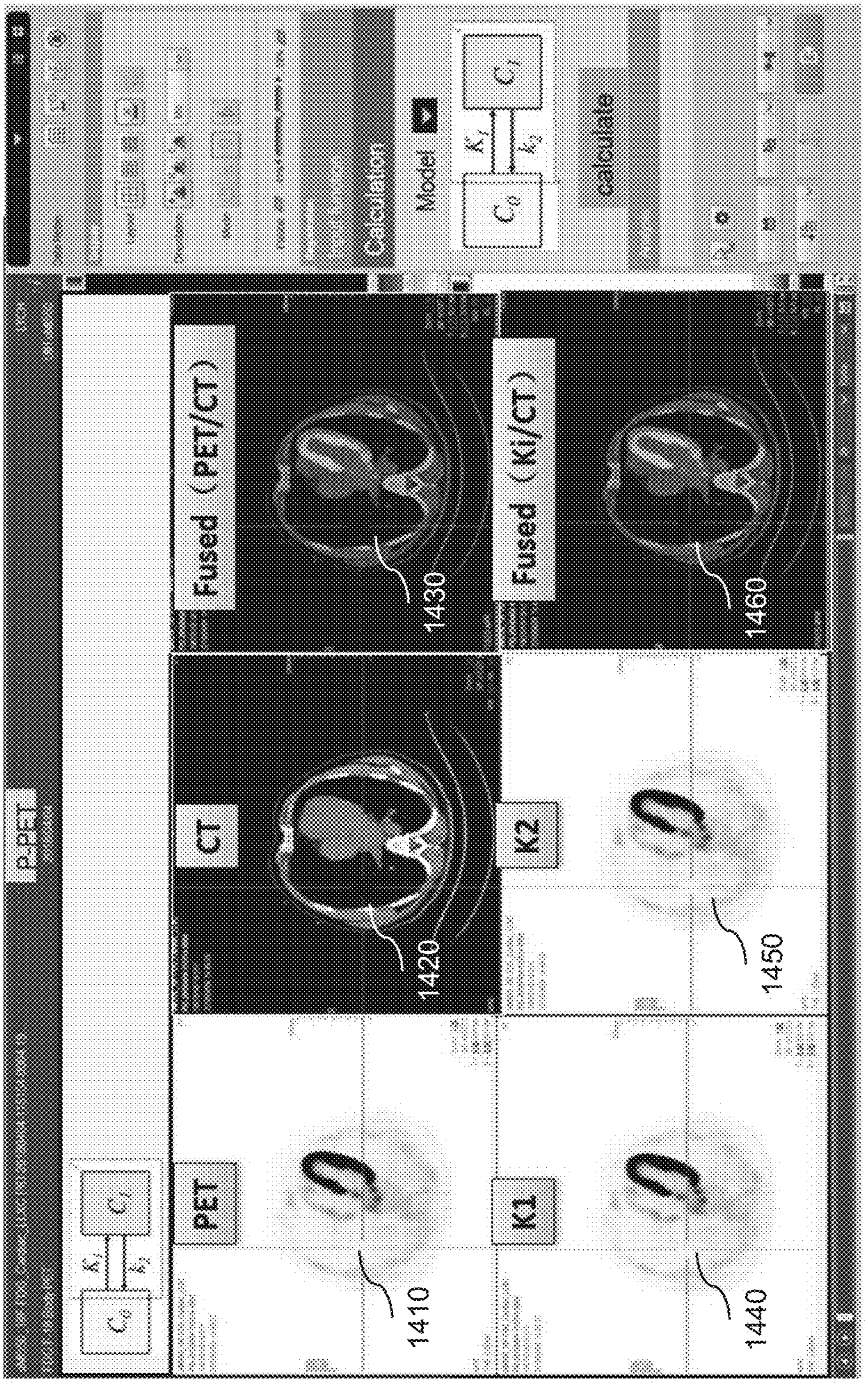
FIG. 14 is a schematic diagram illustrating an exemplary second interface corresponding to a two-compartment model according to some embodiments of the present disclosure.

For example, FIG. 14 is a schematic diagram illustrating an exemplary second interface corresponding to a two-compartment model according to some embodiments of the present disclosure. As shown in FIG. 14, the target model is the two-compartment model including parameters K1 and K2. The second interface 1400 may include six regions used to display a PET image 1410, a CT image 1420, fused images 1430 and 1460, a parameter image 1440 corresponding to the parameter K1, and a parameter image 1450 corresponding to the parameter K2. The fused image 1430 may be generated based on a fusion of the PET image 1410 and the CT image 1420. The fused image 1460 may be generated based on a fusion of the CT image 1420 and one of the parameter image 1440 or the parameter image 1450.

Figure 15:
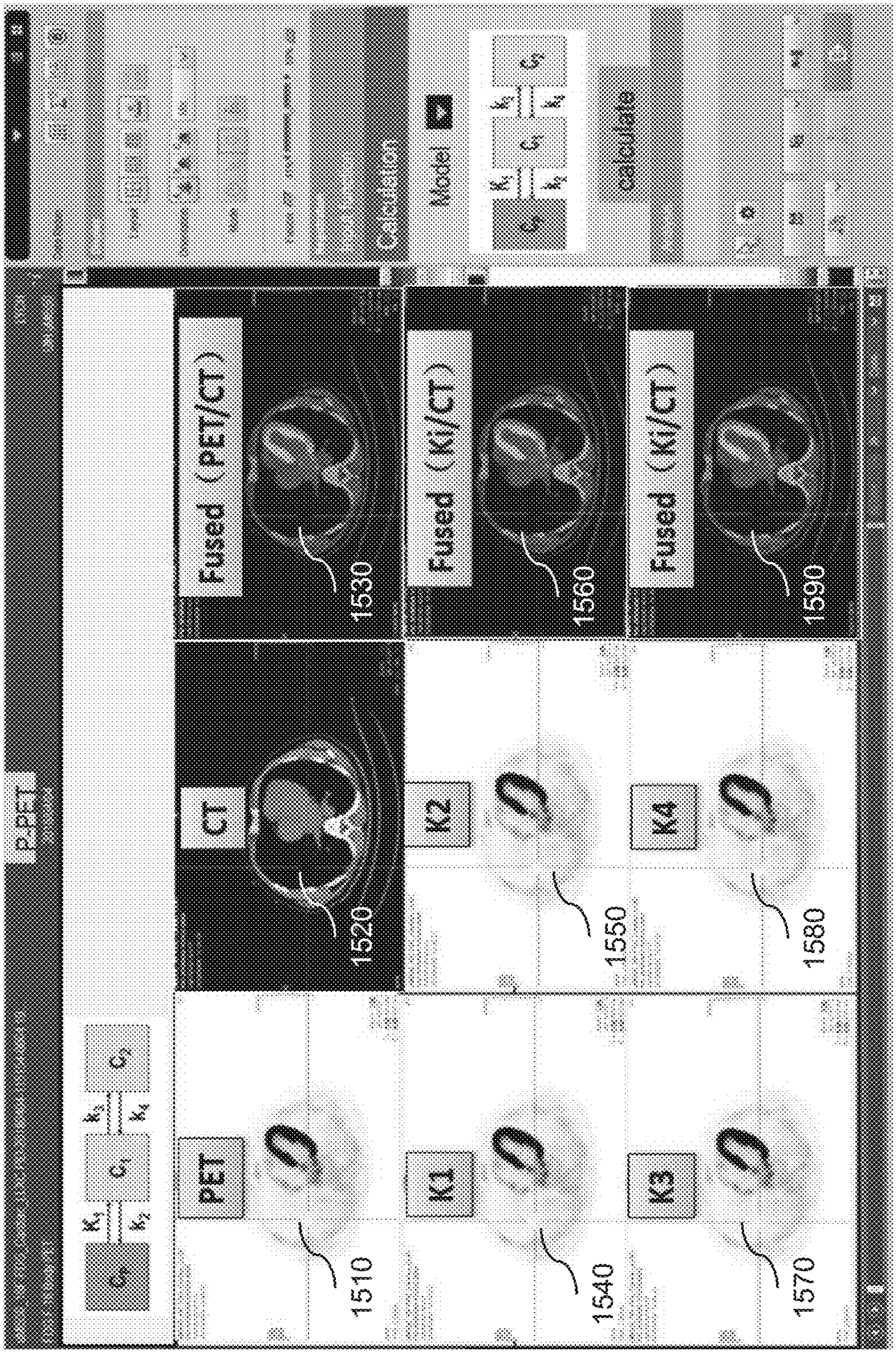
FIG. 15 is a schematic diagram illustrating an exemplary second interface corresponding to a three-compartment model according to some embodiments of the present disclosure.

As another example, FIG. 15 is a schematic diagram illustrating an exemplary second interface corresponding to a three-compartment model according to some embodiments of the present disclosure. As shown in FIG. 15, the target model is the three-compartment model including parameters K1, K2, K3, and K4. The second interface 1500 may include nine regions used to display a PET image 1510, a CT image 1520, fused images 1530, 1560, and 1590, a parameter image 1540 corresponding to the parameter K1, a parameter image 1550 corresponding to the parameter K2, a parameter image 1570 corresponding to the parameter K3, and a parameter image 1580 corresponding to the parameter K4. The fused image 1530 may be generated based on a fusion of the PET image 1510 and the CT image 1520. The fused image 1560 may be generated based on a fusion of the CT image 1520 and one of the parameter image 1540 or the parameter image 1550. The fused image 1590 may be generated based on a fusion of the CT image 1520 and one of the parameter image 1570 or the parameter image 1580.

In some embodiments, the first interface and/or the second interface may be displayed via any suitable software (e.g., a uKinetic software).

Figure 16:
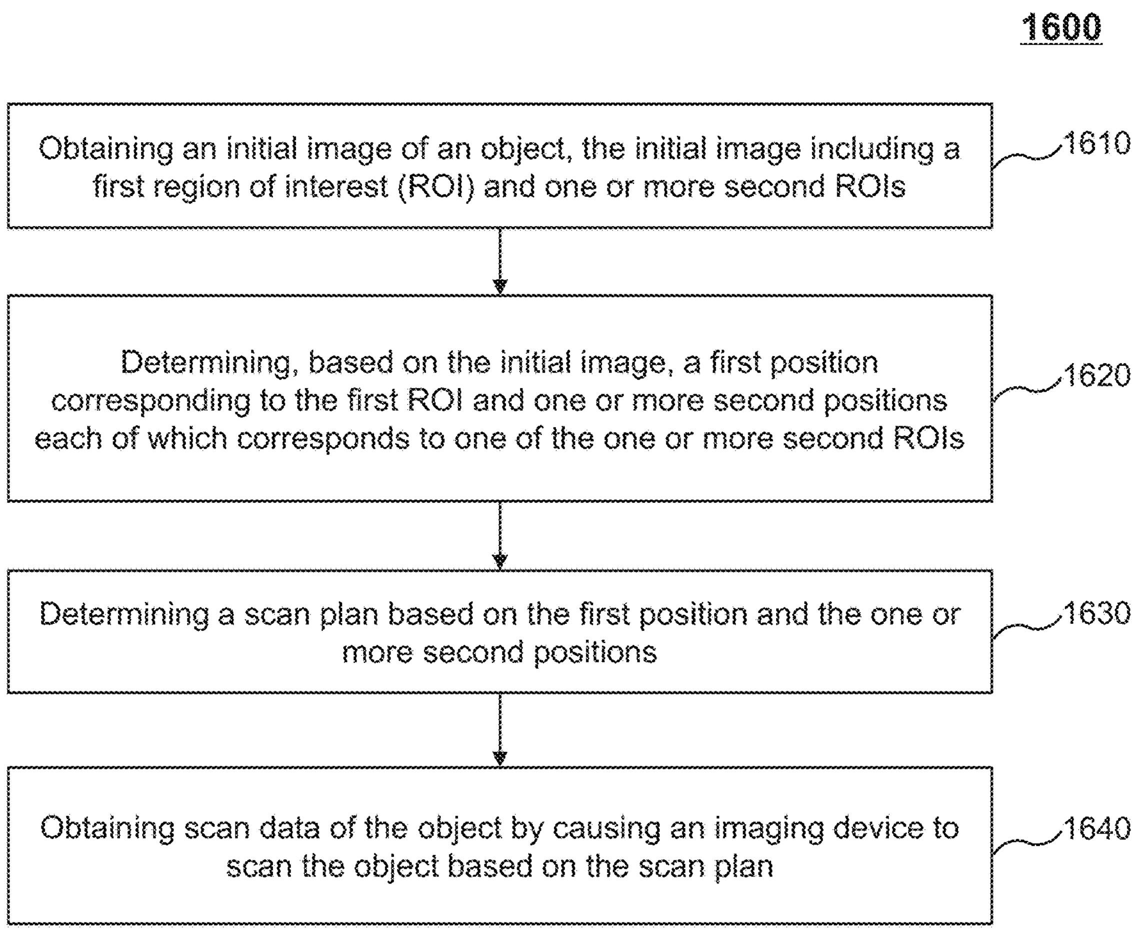
FIG. 16 is a flowchart illustrating an exemplary process for medical imaging according to some embodiments of the present disclosure.

FIG. 16 is a flowchart illustrating an exemplary process for medical imaging according to some embodiments of the present disclosure. In some embodiments, process 1600 may be executed by the medical imaging system 100. For example, the process 1600 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 1600. The operations of the illustrated process presented below are intended to be illustrative. In some embodiments, the process 1600 may be accomplished with one or more additional operations not described and/or without one or more of the operations discussed. Additionally, the order of the operations of process 1600 illustrated in FIG. 16 and described below is not intended to be limiting.

In 1610, the processing device 140 (e.g., the first obtaining module 310 illustrated in FIG. 3, the processor 220 illustrated in FIG. 2) may obtain an initial image (e.g., a scout view) of an object (e.g., a human body).

In some embodiments, the initial image may include a computed tomography (CT) image (e.g., a CT plain scan image), a PET image, a SPECT Image, a radiotherapy radiographic image (e.g., digital radiography), an MR image, an X-ray image, a fluoroscopy image, an ultrasound image, or the like, or a combination thereof.

In some embodiments, the initial image may include a first region of interest (ROI) and one or more second ROIs. The first ROI may be used as a reference for treatment or analysis associated with a tissue or organ. Merely by way of example, the first ROI may include one or more blood pool regions (e.g., aortic blood pools). The one or more second ROIs may include tissue(s) or organ(s) of the object to be scanned according to scan requirements or medical requirements. For example, the one or more second ROIs may include tissue(s) or organ(s) that need treatment and/or other tissue(s) or organ(s) close to the tissue(s) or organ(s) that need treatment. As another example, the one or more second ROIs may include tissue(s) or organ(s) including at least part of a malignant tissue (e.g., a tumor, a cancer-ridden organ, or a non-cancerous target of radiation therapy). As a further example, the one or more second ROIs may include the object's heart, lungs, liver, stomach, pelvis, etc.

In some embodiments, the processing device 140 may determine the first ROI and/or the one or more second ROI in the initial image by using a trained machine learning model. Specifically, the processing device 140 may input the initial image into the trained machine learning model and determine the first ROI and/or the one or more second ROI based on an output of the trained machine learning model. In some embodiments, the trained machine learning model refers to a model or an algorithm for extracting an ROI from an image. Merely by way of example, the trained machine learning model may include a trained neural network model, for example, a deep neural network (DNN) model, a convolutional neural network (CNN) model, a recurrent neural network (RNN) model, a feature pyramid network (FPN) model, or the like, or any combination thereof.

In some embodiments, the trained machine learning model may include an image segmentation algorithm. Exemplary image segmentation algorithm may include a thresholding segmentation algorithm, a compression-based algorithm, an edge detection algorithm, a machine learning-based segmentation algorithm, or the like, or any combination thereof. Exemplary machine learning-based segmentation algorithms may include a 3D U-Net algorithm, a Res-UNet algorithm, a Dense-UNet algorithm, a CNN-based recursive residual image segmentation network algorithm, etc.

In some embodiments, the first ROI and/or the one or more second ROI in the initial image may be manually determined by an operator (e.g., a doctor). For example, the operator may manually sketch the first ROI and/or the one or more second ROI in the initial image via a user interface. In some embodiments, the first ROI and/or the one or more second ROI may be segmented from the initial image by the processing device 140 automatically using an image segmentation algorithm. Exemplary image segmentation algorithm may include a thresholding segmentation algorithm, a compression-based algorithm, an edge detection algorithm, a machine learning-based segmentation algorithm, or the like, or any combination thereof.

In some embodiments, the processing device 140 may direct the imaging device 110 to perform a scan (e.g., a PET scan) on the object and determine the initial image based on scanning data obtained from the imaging device 110. In some embodiments, the initial image may be previously determined and stored in a storage device (e.g., the storage device 150, the storage 230, an external storage device) or an external system (e.g., a picture archiving and communication system (PACS)). The processing device 140 may obtain the initial image from the storage device or the external system directly or via a network (e.g., the network 120).

In 1620, the processing device 140 (e.g., the first determination module 320 illustrated in FIG. 3, the processor 220 illustrated in FIG. 2) may determine, based on the initial image, a first position corresponding to the first ROI and one or more second positions each of which corresponds to one of the one or more second ROIs.

In some embodiments, the first position or the second position refers to a position of a couch (e.g., the couch 114) on which the object is supported relative to an imaging device (e.g., the imaging device 110). The first position may be a scanning position (e.g., an optimal scanning position (e.g., a center of a scanning FOV of the imaging device)) for the imaging device to scan the first ROI. The second position may be a scanning position (e.g., an optimal scanning position (e.g., a center of a scanning FOV of the imaging device)) for the imaging device to scan a corresponding second ROI.

In some embodiments, the processing device 140 may determine the first position and/or the one or more second positions by using a trained machine learning model. Specifically, the processing device 140 may input the initial image into the trained machine learning model and determine the first position and/or the one or more second positions based on an output of the trained machine learning model.

In 1630, the processing device 140 (e.g., the second obtaining module 330 illustrated in FIG. 3, the processor 220 illustrated in FIG. 2) may determine a scan plan based on the first position and the one or more second positions.

In some embodiments, the scan plan may include the first position, the one or more second positions, a scan range (also referred to as a "scan region") of each of the first ROI and the one or more second ROIs, a scan parameter (e.g., a size) associated with an overlapping region of scanning regions corresponding to two adjacent second ROIs, or the like, or a combination thereof.

In some embodiments, the processing device 140 may determine the scan plan based on the first position, the one or more second positions, and a parameter associated with a drug (e.g., the tracer species) that is injected into the object. The parameter associated with the drug may include a type of the drug, a metabolism rate of the drug in the object, a flow rate of the drug in the object, or the like, or any combination thereof. Accordingly, the scan plan may further include a moving speed of the object among the first position and the one or more second positions, for example, a moving speed of the object from a first position to a second position, a moving speed of the object from a second position to a next second position, etc. Specifically, the processing device 140 may determine the moving speed of the object among the first position and the one or more second positions based on the metabolism rate and/or the flow rate of the drug in the object. Merely by way of example, the faster the metabolism or the flow rate of the drug is, the faster the moving speed of the object among the first position and the one or more second positions may be.

In some embodiments, the scan plan may further include a scan time. The scan time may include a time when the couch or the imaging device starts to move, a time when the couch or the imaging device reaches the first position or the one or more second positions, a time period (also referred to as a "scan time period") during which the couch or the imaging device stays at the first position or the one or more second positions, or the like, or any combination thereof. In some embodiments, the processing device 140 may determine the scan time based on the first position, the one or more second positions, the moving speed of the object among the first position and the one or more second positions, and the parameter associated with a drug.

In some embodiments, the processing device 140 may show the scan plan to the operator via a display (e.g., the display 240). The operator may manually revise the scan plan (e.g., adjusting the size of the overlapping region) through an input device (e.g., the I/O 260).

In 1640, the processing device 140 (e.g., the second obtaining module 330 illustrated in FIG. 3, the processor 220 illustrated in FIG. 2) may obtain scan data of the object by causing an imaging device to scan the object based on the scan plan.

In some embodiments, the processing device 140 may move the couch (e.g., the couch 114) or the imaging device (e.g., the imaging device 110) until a current relative position of the couch and the imaging device reaches the first position at which the first ROI is in the scanning FOV (e.g., a center of the scanning FOV) of the imaging device. Then the processing device 140 may start the imaging device to scan the object to obtain the scan data of the first ROI. After the scan data of the first ROI is obtained, the processing device 140 may further move the couch or the imaging device until the current relative position of the couch and the imaging device reaches a second position (i.e., moves from the first position to the second position) at which a corresponding second ROI is in the scanning FOV (e.g., a center of the FOV) of the imaging device. Then the processing device 140 may start the imaging device to scan the object to obtain the scan data of the second ROI. After the scan data of the second ROI is obtained, the processing device 140 may further change move the couch or the imaging device until the current relative position of the couch and the imaging device reaches a next second position (i.e., moves from the current second position to a next second position) at which a next corresponding second ROI is in the scanning FOV (e.g., a center of the FOV) of the imaging device, and then obtain the scan data of the next second ROI until the scan data of the last of the one or more second ROIs is obtained.

In the embodiments of the present disclosure, the first position and the one or more second positions may be determined automatically, and the scanning of the object may be automatically performed based on the first position and the one or more second positions, which enables the object to be located in a more accurate scanning position, reduces the workload of the operator, saves human resources, improves the work efficiency, and avoids the low imaging accuracy caused by subjective factors such as inexperience of the operator, thereby reducing the probability that the object needs to be rescanned, reducing the radiation dose received by the patient, and protecting the object's health.

In some embodiments, when multiple second ROIs (e.g., lungs, liver, and pelvis) of the object need to be imaged, boundaries of the second ROIs in a scanned image may not be clear enough. Accordingly, in the present disclosure, an overlapping region of scanning regions corresponding two adjacent second ROIs may be determined and added in the scan plan. During the scanning process, the overlapping region may be scanned twice and scan data obtained from the two scans may be superimposed to determine the final scanned image, which can improve the definition of the boundaries of the two adjacent second ROIs. In some embodiments, a size of the overlapping region or a percentage of the overlapping region in any one of the scanning regions corresponding to the two adjacent second ROIs may be larger than a predetermined threshold. For example, the size of the overlapping region may be larger than 600 mm*200 mm, 500 mm*100 mm, 400 mm*100 mm, 400 mm*50 mm etc. As another example, the percentage of the overlapping region in any one of the scanning regions corresponding to the two adjacent second ROIs may be larger than a predetermined percentage (e.g., 5%, 10%, 20%, 25%).

Generally, during the scanning, it is necessary to ensure that scan data collection is started at the moment when the drug is injected into the object's body to ensure an accurate scanning process and an accurate scanning result. Accordingly, in some embodiments of the present disclosure, the processing device 140 may start the scan data collection through a preset manner while injecting the drug into the object. The preset manner may include starting the scan data collection through foot pedal sensing, gesture recognition, voice recognition, brain wave recognition, a VR/AR device, a device accessory, or the like, or any combination thereof.

In some embodiments, a foot pedal sensing device may be set up around the imaging device (e.g., the imaging device 110), and the operator may immediately start the scan data collection by touching the foot pedal device.

In some embodiments, a gesture sensing device may be provided around the imaging device. The gesture sensing device may automatically recognize the action of drug injection, and start the scan data collection immediately upon recognizing the action of drug injection.

In some embodiments, a voice recognition device may be provided around the imaging device. The voice recognition device may automatically recognize the operator's voice command to start drug injection, and start the scan data collection immediately upon recognizing the voice command. In addition, the operator may be instructed in drug injection by the voice recognition device. Specifically, the voice recognition device may inform the operator the start time of the scan data collection, and require the operator to perform the drug injection at the time when the scan data collection starts. Merely by way of example, the voice recognition device may inform the operator by means of a countdown reminder for the start of the scan data collection, a prompt sound at the moment when the scan data collection starts, etc.

In some embodiments, a brain wave recognition device may be set on the operator to recognize the brain waves of the operator, and to synchronously start the scan data collection based on the recognized collection instruction issued by the operator's brain.

In some embodiments, an operator of the imaging device and an operator of the drug injection may wear synchronous VR/AR devices. The operator of the imaging device may recognize the injection action through the synchronous VR/AR devices, and start the scan data collection synchronously.

In some embodiments, the drug injection and the scan data collection may be started synchronously through a device accessory (e.g., a button, a key, a switch). For example, a button to start the scan data collection may be provided within an operating range of the operator, and the operator may start the scan data collection through the button while injecting the drug.

In some embodiments, the drug injection and the scan data collection may be started synchronously in other ways. For example, the operator may start the scan data collection by directly touching a touch screen covered by a disposable antibacterial cover.

In the embodiments of the present disclosure, the drug injection and the scan data collection may be started synchronously through multiple preset manners, which avoids or reduces the generation of the invalid scan, thereby avoiding or reducing the errors in subsequent data analysis and processing.

It should be noted that the above description of the process 1600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 17:
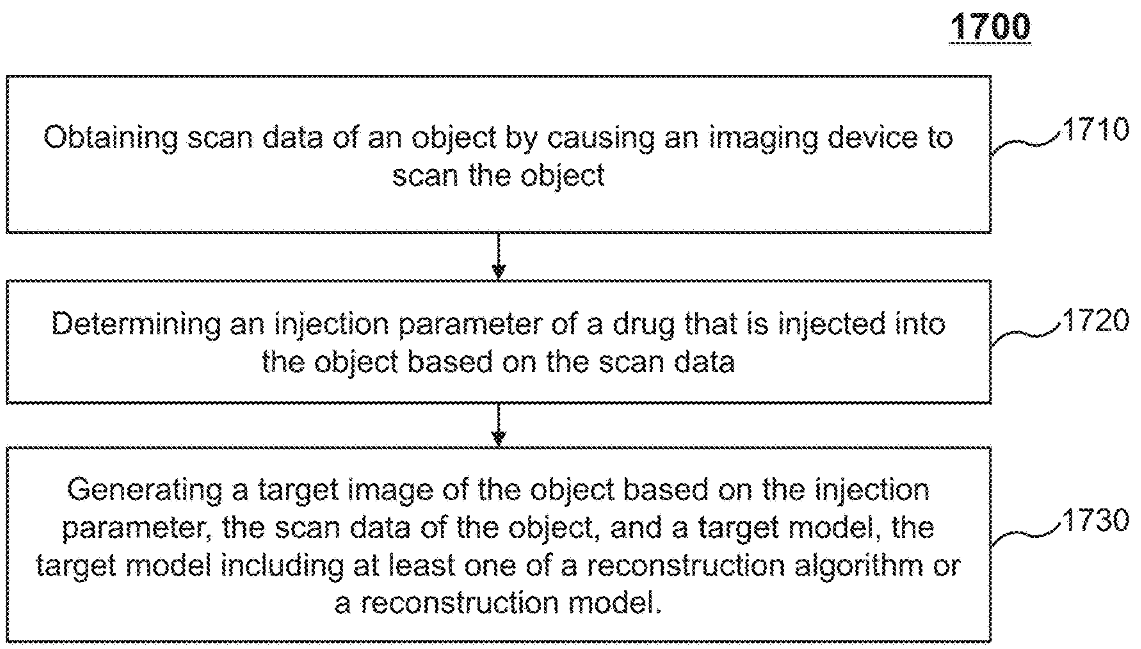
FIG. 17 is a flowchart illustrating an exemplary process for medical imaging according to some embodiments of the present disclosure.

FIG. 17 is a flowchart illustrating an exemplary process for medical imaging according to some embodiments of the present disclosure. In some embodiments, process 1700 may be executed by the medical imaging system 100. For example, the process 1700 may be implemented as a set of instructions (e.g., an application) stored in a storage device (e.g., the storage device 150, the storage 230). In some embodiments, the processing device 140 (e.g., the processor 220 of the computing device 200 and/or one or more modules illustrated in FIG. 3) may execute the set of instructions and may accordingly be directed to perform the process 1700. The operations of the illustrated process presented below are intended to be illustrative. In some embodiments, the process 1700 may be accomplished with one or more additional operations not described and/or without one or more of the operations discussed. Additionally, the order of the operations of process 1700 illustrated in FIG. 17 and described below is not intended to be limiting.

In 1710, the processing device 140 (e.g., the second obtaining module 330 illustrated in FIG. 3, the processor 220 illustrated in FIG. 2) may obtain scan data of an object by causing an imaging device to scan the object.

In some embodiments, the processing device 140 may direct the imaging device 110 to perform a scan (e.g., a PET scan) on the object to obtain the scan data of the object. In some embodiments, the scan data of the object may be previously obtained and stored in a storage device (e.g., the storage device 150, the storage 230, an external storage device) or an external system (e.g., a picture archiving and communication system (PACS)). The processing device 140 may obtain the scan data of the object from the storage device or the external system directly or via a network (e.g., the network 120).

In 1720, the processing device 140 (e.g., the second determination module 340 illustrated in FIG. 3, the processor 220 illustrated in FIG. 2) may determine an injection parameter of the drug that is injected into the object based on the scan data.

In some embodiments, the scan data may include a count of pairs of photons detected and/or registered by detectors, position information associated with multiple coincidence events, time information (e.g., a time when a pair of photons reaches the detectors, a time when a pair of photons appears) associated with multiple coincidence events, or the like, or any combination thereof. As described in connection with FIG. 1, a coincidence event may indicate a pair of photons detected by detectors surrounding the object within a preset time window.

In some embodiments, the injection parameter of the drug may include an injection dose of the drug, an injection time of the drug, or the like, or a combination thereof.

In some embodiments, the processing device 140 may determine a count of the coincidence events for the object based on the scan data and further determine the injection dose of the drug based on the count of the coincidence events. More descriptions regarding the determining of the injection dose of the drug may be found elsewhere in the present disclosure, for example, FIG. 8 and the descriptions thereof.

In some embodiments, the processing device 140 may determine a plurality of initial reconstruction images based on at least a portion of the scan data according to a preset temporal frequency and further determine the injection time of the drug based on the plurality of initial reconstruction images. More descriptions regarding the determining of the injection time of the drug may be found elsewhere in the present disclosure, for example, FIG. 9 and the descriptions thereof.

In the embodiments of the present disclosure, the injection time and the injection dose of the drug may be automatically determined, which avoids the operator manually entering the injection time and injection dose, thereby avoiding or reducing manual enter errors, reducing the workload of the operator, improving the accuracy of the determination of the injection time and the injection dose, and improving the efficiency and accuracy of the medical imaging.

In 1730, the processing device 140 (e.g., the generation module 350 illustrated in FIG. 3, the processor 220 illustrated in FIG. 2) may generate a target image of the object based on the injection parameter, the scan data of the object, and a target model.

In some embodiments, the processing device 140 may input the injection parameter and the scan data into the target model and determine the target image of the object based on an output of the target model. In some embodiments, the target model may include a reconstruction algorithm, a reconstruction model, a kinetic model, or the like, or any combination thereof. The reconstruction algorithm may include a time of flight (TOF)-based reconstruction algorithm, a deep learning-based reconstruction algorithm, or the like, or any combination thereof. The reconstruction model may include, for example, a trained machine learning model (e.g., a trained neural network model). The kinetic model may indicate a metabolism situation of the drug injected into the object. The kinetic model may include, for example, a compartment model. The compartment model may include a two compartment model, a three compartment model, a four compartment model, or the like, or any combination thereof.

It should be noted that the above description of the process 1700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.), or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in a baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction-performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer, and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:

at least one storage device including a set of instructions; and at least one processor in communication with the at least one storage device, wherein when executing the set of instructions, the at least one processor causes the system to perform operations including:

obtaining an initial image of an object, the initial image including a first region of interest (ROI) and one or more second ROIs;

determining, based on the initial image, a first position corresponding to the first ROI and one or more second positions each of which corresponds to one of the one or more second ROIs;

obtaining scan data of the object by causing an imaging device to scan the object based on the first position and the one or more second positions;

determining an injection parameter of a drug that is injected into the object based on the scan data by:

determining a count of coincidence events for the object based on the scan data, a coincidence event indicating a pair of photons detected by detectors surrounding the object within a preset time window; and determining an injection dose of the drug based on the count of the coincidence events; and generating a target image of the object based on the injection parameter and the scan data of the object.

2. The system of claim 1, wherein the obtaining the scan data of the object by causing the imaging device to scan the object based on the first position and the one or more second positions includes:

determining a scan plan based on the first position and the one or more second positions, the scan plan at least including a scan parameter associated with an overlapping region of scanning regions corresponding to two adjacent second ROIs; and obtaining the scan data of the object by causing the imaging device to scan the object based on the scan plan.

3. The system of claim 1, wherein the obtaining the scan data of the object by causing the imaging device to scan the object based on the first position and the one or more second positions includes:

determining a scan plan based on the first position, the one or more second positions, and a parameter associated with the drug, the scan plan at least including a moving speed of the object among the first position and the one or more second positions; and obtaining the scan data of the object by causing the imaging device to scan the object based on the scan plan.

4. The system of claim 1, wherein the determining the count of the coincidence events includes:

determining the count of the coincidence events by correcting an initial count of the coincidence events based on a decay correction function.

5. The system of claim 1, wherein the determining the injection parameter of the drug that is injected into the object based on the scan data includes:

determining a plurality of initial reconstruction images based on at least a portion of the scan data according to a preset temporal frequency; and determining an injection time of the drug based on the plurality of initial reconstruction images.

6. The system of claim 5, wherein the determining the injection time of the drug based on the plurality of initial reconstruction images includes:

for each of the plurality of initial reconstruction images, determining pixel values associated with a target region;

determining, from the plurality of initial reconstruction images, a target reconstruction image based on the pixel values corresponding to the plurality of initial reconstruction images respectively, the target reconstruction image corresponding to target pixel values indicating that the target reconstruction image is the first image, among the plurality of initial reconstruction images, that indicates an occurrence of the drug; and designating an acquisition time associated with the target reconstruction image as the injection time of the drug.

7. The system of claim 1, wherein the generating the target image of the object based on the injection parameter and the scan data of the object includes:

generating the target image of the object based on the injection parameter, the scan data of the object, and a target model, wherein the target model further includes at least one of a reconstruction algorithm, a reconstruction model, or a kinetic model, and the kinetic model indicates a metabolism situation of the drug injected into the object.

8. The system of claim 7, wherein the operations further include:

causing a display device to display a first interface, the first interface including a plurality of preset models each of which indicates a conversion relationship among parameters of the preset model;

in response to a trigger instruction, determining the target model from the plurality of preset models; and causing the display device to display a second interface based on the target model, the second interface including at least one region used to display at least one parameter image each of which is related to a parameter of the target model.

9. The system of claim 8, wherein the plurality of preset models includes a compartment model, the compartment model including at least one of a two-compartment model, a three-compartment model, or a four-compartment model.

10. A method for medical imaging, the method being implemented on a computing device including at least one processor and at least one storage device, the method comprising:

obtaining an initial image of an object, the initial image including a first region of interest (ROI) and one or more second ROIs;

determining, based on the initial image, a first position corresponding to the first ROI and one or more second positions each of which corresponds to one of the one or more second ROIs;

obtaining scan data of the object by causing an imaging device to scan the object based on the first position and the one or more second positions;

determining an injection parameter of a drug that is injected into the object based on the scan data by:

determining a count of coincidence events for the object based on the scan data, a coincidence event indicating a pair of photons detected by detectors surrounding the object within a preset time window; and determining an injection dose of the drug based on the count of the coincidence events; and generating a target image of the object based on the injection parameter and the scan data of the object.

11. The method of claim 10, wherein the obtaining the scan data of the object by causing the imaging device to scan the object based on the first position and the one or more second positions includes:

determining a scan plan based on the first position and the one or more second positions, the scan plan at least including a scan parameter associated with an overlapping region of scanning regions corresponding to two adjacent second ROIs; and obtaining the scan data of the object by causing the imaging device to scan the object based on the scan plan.

12. The method of claim 10, wherein the obtaining the scan data of the object by causing the imaging device to scan the object based on the first position and the one or more second positions includes:

determining a scan plan based on the first position, the one or more second positions, and a parameter associated with the drug, the scan plan at least including a moving speed of the object among the first position and the one or more second positions; and obtaining the scan data of the object by causing the imaging device to scan the object based on the scan plan.

13. The method of claim 10, wherein the determining the count of the coincidence events includes:

determining the count of the coincidence events by correcting an initial count of the coincidence events based on a decay correction function.

14. The method of claim 10, wherein the determining the injection parameter of the drug that is injected into the object based on the scan data includes:

determining a plurality of initial reconstruction images based on at least a portion of the scan data according to a preset temporal frequency; and determining an injection time of the drug based on the plurality of initial reconstruction images.

15. The method of claim 14, wherein the determining the injection time of the drug based on the plurality of initial reconstruction images includes:

for each of the plurality of initial reconstruction images, determining pixel values associated with a target region;

determining, from the plurality of initial reconstruction images, a target reconstruction image based on the pixel values corresponding to the plurality of initial reconstruction images respectively, the target reconstruction image corresponding to target pixel values indicating that the target reconstruction image is the first image, among the plurality of initial reconstruction images, that indicates an occurrence of the drug; and designating an acquisition time associated with the target reconstruction image as the injection time of the drug.

16. The method of claim 10, wherein the generating the target image of the object based on the injection parameter and the scan data of the object includes:

generating the target image of the object based on the injection parameter, the scan data of the object, and a target model, wherein the target model further includes at least one of a reconstruction algorithm, a reconstruction model, or a kinetic model, and the kinetic model indicates a metabolism situation of the drug injected into the object.

17. The method of claim 16, wherein the method further includes:

causing a display device to display a first interface, the first interface including a plurality of preset models each of which indicates a conversion relationship among parameters of the preset model;

in response to a trigger instruction, determining the target model from the plurality of preset models; and causing the display device to display a second interface based on the target model, the second interface including at least one region used to display at least one parameter image each of which is related to a parameter of the target model.

18. A system, comprising:

at least one storage device including a set of instructions; and at least one processor in communication with the at least one storage device, wherein when executing the set of instructions, the at least one processor causes the system to perform operations including:

obtaining an initial image of an object, the initial image including a first region of interest (ROI) and one or more second ROIs;

determining, based on the initial image, a first position corresponding to the first ROI and one or more second positions each of which corresponds to one of the one or more second ROIs;

determining a scan plan based on the first position and the one or more second positions;

obtaining scan data of the object by causing an imaging device to scan the object based on the scan plan;

determining an injection parameter of a drug that is injected into the object based on the scan data by:

determining a count of coincidence events for the object based on the scan data, a coincidence event indicating a pair of photons detected by detectors surrounding the object within a preset time window; and determining an injection dose of the drug based on the count of the coincidence events; and generating a target image of the object based on the injection parameter and the scan data of the object.

* * * * *